United States Patent
Bowles et al.

(10) Patent No.: US 11,074,538 B2
(45) Date of Patent: *Jul. 27, 2021

(54) ADAPTIVE ALERTNESS TESTING SYSTEM AND METHOD

(71) Applicant: Predictive Safety SRP, Inc., Centennial, CO (US)

(72) Inventors: Henry M. Bowles, Alameda, CA (US); Marcus T. Wichmann, Aurora, CO (US); Darren B. Chamberlin, Mulgoa (AU)

(73) Assignee: Predictive Safety SRP, Inc., Centennial, CO (US)

( * ) Notice: Subject to any disclaimer, the term of this patent is extended or adjusted under 35 U.S.C. 154(b) by 631 days.

This patent is subject to a terminal disclaimer.

(21) Appl. No.: 15/625,908

(22) Filed: Jun. 16, 2017

(65) Prior Publication Data

US 2017/0360349 A1    Dec. 21, 2017

Related U.S. Application Data

(60) Provisional application No. 62/351,665, filed on Jun. 17, 2016.

(51) Int. Cl.
*A61B 5/00* (2006.01)
*G06Q 10/06* (2012.01)
(Continued)

(52) U.S. Cl.
CPC ..... *G06Q 10/06398* (2013.01); *A61B 5/0002* (2013.01); *A61B 5/0022* (2013.01);
(Continued)

(58) Field of Classification Search
None
See application file for complete search history.

(56) References Cited

U.S. PATENT DOCUMENTS

| 4,755,140 A | 7/1988 | Rimland |
| 4,770,636 A | 9/1988 | Buschke |

(Continued)

FOREIGN PATENT DOCUMENTS

| CN | 104063925 A | 9/2014 |
| CN | 104808901 A | 7/2015 |

(Continued)

OTHER PUBLICATIONS

International Search Report and Written Opinion dated Sep. 1, 2017 in counterpart International Application Serial No. PCT/US2017/038039.

(Continued)

*Primary Examiner* — Bruk A Gebremichael
(74) *Attorney, Agent, or Firm* — Brian J. Colandreo; Heath M. Sargeant; Holland & Knight LLP

(57) ABSTRACT

A method, computer program product, and computing system for monitoring one or more environmental variables concerning a client electronic device configured to administer an alertness test to a user. A disrupter is selected for inclusion within the alertness test based, at least in part, upon the one or more environmental variables concerning the client electronic device. The alertness test is administered to the user.

12 Claims, 11 Drawing Sheets

(51) Int. Cl.

| | | |
|---|---|---|
| *G06F 3/0481* | (2013.01) | |
| *G06F 3/0484* | (2013.01) | |
| *G08B 21/06* | (2006.01) | |
| *H04W 12/08* | (2021.01) | |
| *G07C 9/20* | (2020.01) | |
| *G07C 9/28* | (2020.01) | |
| *G07C 9/30* | (2020.01) | |
| *G06F 21/36* | (2013.01) | |
| *H04L 29/06* | (2006.01) | |
| *A61B 5/18* | (2006.01) | |
| *G06Q 10/10* | (2012.01) | |
| *G06F 3/0482* | (2013.01) | |
| *G09B 5/06* | (2006.01) | |
| *G09B 7/10* | (2006.01) | |
| *A61B 5/11* | (2006.01) | |
| *A61B 5/16* | (2006.01) | |
| *G09B 7/00* | (2006.01) | |
| *G08B 21/02* | (2006.01) | |
| *G16H 15/00* | (2018.01) | |
| *A61B 5/0205* | (2006.01) | |
| *A61B 5/145* | (2006.01) | |
| *G16H 10/20* | (2018.01) | |
| *H04W 12/63* | (2021.01) | |
| *H04W 80/12* | (2009.01) | |
| *H04W 84/04* | (2009.01) | |
| *A61B 5/024* | (2006.01) | |

(52) U.S. Cl.
CPC .......... *A61B 5/0077* (2013.01); *A61B 5/0205* (2013.01); *A61B 5/1112* (2013.01); *A61B 5/14542* (2013.01); *A61B 5/16* (2013.01); *A61B 5/162* (2013.01); *A61B 5/165* (2013.01); *A61B 5/18* (2013.01); *A61B 5/4064* (2013.01); *A61B 5/4088* (2013.01); *A61B 5/6898* (2013.01); *G06F 3/0482* (2013.01); *G06F 3/0484* (2013.01); *G06F 3/04812* (2013.01); *G06F 21/36* (2013.01); *G06Q 10/1091* (2013.01); *G07C 9/20* (2020.01); *G07C 9/28* (2020.01); *G07C 9/30* (2020.01); *G08B 21/02* (2013.01); *G08B 21/06* (2013.01); *G09B 5/065* (2013.01); *G09B 7/00* (2013.01); *G09B 7/10* (2013.01); *G16H 10/20* (2018.01); *G16H 15/00* (2018.01); *H04L 63/10* (2013.01); *H04W 12/08* (2013.01); *A61B 5/024* (2013.01); *A61B 5/14532* (2013.01); *A61B 5/4857* (2013.01); *A61B 2503/20* (2013.01); *A61B 2560/0247* (2013.01); *A61B 2562/0204* (2013.01); *H04W 12/63* (2021.01); *H04W 80/12* (2013.01); *H04W 84/042* (2013.01)

(56) References Cited

U.S. PATENT DOCUMENTS

| | | |
|---|---|---|
| 4,978,303 A | 12/1990 | Lampbell |
| 5,295,491 A | 3/1994 | Gevins |
| 5,595,488 A | 1/1997 | Gozlan et al. |
| 5,774,525 A | 6/1998 | Kanevsky et al. |
| 5,940,801 A | 8/1999 | Brown |
| 6,113,538 A | 9/2000 | Bowles et al. |
| 6,122,536 A | 9/2000 | Sun et al. |
| 6,265,978 B1 | 7/2001 | Atlas |
| 6,485,417 B1 | 11/2002 | Bowles et al. |
| 6,553,252 B2 | 4/2003 | Balkin et al. |
| 6,632,174 B1 | 10/2003 | Breznitz |
| 6,743,022 B1 | 6/2004 | Sarel |
| 6,743,171 B1 | 6/2004 | Bowles et al. |
| 6,950,532 B1 | 9/2005 | Schumann et al. |
| 6,985,069 B2 | 1/2006 | Pinter et al. |
| 7,027,621 B1 | 4/2006 | Prokoski |
| 7,087,015 B1 | 8/2006 | Comrie et al. |
| 7,488,294 B2 | 2/2009 | Torch |
| 8,044,772 B1 | 10/2011 | Roe |
| 8,652,041 B2 | 2/2014 | Moore-Ede |
| 8,725,311 B1 | 5/2014 | Breed |
| 8,781,796 B2 | 7/2014 | Mott et al. |
| 8,812,428 B2 | 8/2014 | Mollicone et al. |
| 9,033,892 B2 | 5/2015 | Su et al. |
| 9,142,115 B2 | 9/2015 | Tao |
| 9,205,842 B1 | 12/2015 | Fields et al. |
| 9,613,203 B2 | 4/2017 | Jerusalimsky |
| 9,742,751 B2 | 8/2017 | Jakobsson |
| 2002/0143240 A1 | 10/2002 | Teicher et al. |
| 2003/0013981 A1 | 1/2003 | Gevins et al. |
| 2003/0095046 A1 | 5/2003 | Borugian |
| 2004/0210159 A1 | 10/2004 | Kibar |
| 2004/0229198 A1 | 11/2004 | Boyd et al. |
| 2005/0030184 A1 | 2/2005 | Victor |
| 2005/0064375 A1 | 3/2005 | Blank |
| 2005/0065375 A1 | 3/2005 | Benneker et al. |
| 2005/0162965 A1 | 7/2005 | Fukuda et al. |
| 2006/0036868 A1 | 2/2006 | Cicchitto |
| 2007/0120691 A1 | 5/2007 | Braun |
| 2007/0299319 A1 | 12/2007 | Chan et al. |
| 2008/0043201 A1 | 2/2008 | Todd |
| 2008/0084319 A1 | 4/2008 | Fan |
| 2008/0138784 A1 | 6/2008 | Adler |
| 2008/0267425 A1 | 10/2008 | Le Faucher et al. |
| 2008/0309616 A1 | 12/2008 | Massengill |
| 2009/0005652 A1 | 1/2009 | Kurtz |
| 2009/0024050 A1 | 1/2009 | Jung et al. |
| 2009/0112620 A1 | 4/2009 | Jung et al. |
| 2009/0267777 A1 | 10/2009 | Kumar et al. |
| 2010/0228584 A1 | 9/2010 | Nash |
| 2010/0240982 A1 | 9/2010 | Westbrook |
| 2010/0270372 A1 | 10/2010 | Bae |
| 2011/0025611 A1 | 2/2011 | Yoo et al. |
| 2011/0029902 A1 | 2/2011 | Bailey |
| 2011/0040204 A1 | 2/2011 | Ivorra et al. |
| 2011/0150267 A1 | 6/2011 | Snelling et al. |
| 2011/0205167 A1 | 8/2011 | Massengill |
| 2011/0281643 A1 | 11/2011 | Rioux et al. |
| 2011/0304465 A1 | 12/2011 | Boult et al. |
| 2012/0032806 A1 | 2/2012 | Lee |
| 2012/0203464 A1 | 8/2012 | Mollicone et al. |
| 2012/0214143 A1 | 8/2012 | Severson et al. |
| 2012/0232907 A1 | 9/2012 | Ivey |
| 2012/0278766 A1 | 11/2012 | Massengill |
| 2012/0303965 A1 | 11/2012 | Carter |
| 2013/0109944 A1 | 5/2013 | Sparacino et al. |
| 2013/0135109 A1 | 5/2013 | Sharon |
| 2013/0243208 A1 | 9/2013 | Fawer |
| 2013/0318580 A1 | 11/2013 | Gudlavenkatasiva et al. |
| 2014/0160011 A1 | 6/2014 | Park et al. |
| 2014/0198061 A1 | 7/2014 | Chen |
| 2014/0223531 A1 | 8/2014 | Outwater |
| 2014/0223581 A1 | 8/2014 | Mahendrakar et al. |
| 2014/0276130 A1 | 9/2014 | Mirelman et al. |
| 2014/0278586 A1* | 9/2014 | Sanchez .............. G06Q 40/00 705/4 |
| 2015/0007307 A1 | 1/2015 | Grimes et al. |
| 2015/0038855 A1 | 2/2015 | Berckmans et al. |
| 2015/0051508 A1 | 2/2015 | Ghajar et al. |
| 2015/0073289 A1 | 3/2015 | Lim |
| 2015/0095241 A1 | 4/2015 | Edwards |
| 2015/0161876 A1 | 6/2015 | Castillo |
| 2015/0213725 A1 | 7/2015 | Huntley et al. |
| 2015/0339589 A1 | 11/2015 | Fisher |
| 2016/0012218 A1 | 1/2016 | Perna et al. |
| 2016/0071393 A1 | 3/2016 | Kaplan et al. |
| 2016/0103338 A1 | 4/2016 | Hart |
| 2016/0125748 A1 | 5/2016 | Ashford |
| 2016/0148523 A1 | 5/2016 | Winston |
| 2016/0150978 A1 | 6/2016 | Yuen et al. |
| 2016/0163217 A1 | 6/2016 | Harkness |
| 2016/0262608 A1 | 9/2016 | Krueger |
| 2016/0278682 A1 | 9/2016 | Khaligh-Razavi et al. |

(56) References Cited

U.S. PATENT DOCUMENTS

| | | |
|---|---|---|
| 2016/0367180 A1 | 12/2016 | Lunt et al. |
| 2016/0371908 A1 | 12/2016 | Dow et al. |
| 2017/0063858 A1 | 3/2017 | Bandi et al. |
| 2017/0084187 A1 | 3/2017 | Mollicone et al. |
| 2017/0150907 A1 | 6/2017 | Duffy |
| 2019/0012250 A1 | 1/2019 | Kamath |

FOREIGN PATENT DOCUMENTS

| | | | |
|---|---|---|---|
| CN | 105373716 | A | 3/2016 |
| DE | 2500167 | A1 | 7/1976 |
| DE | 10218945 | A1 | 11/2003 |
| DE | 102014208711 | A1 | 3/2009 |
| EP | 1301117 | A2 | 4/2003 |
| EP | 2854409 | A1 | 4/2015 |
| JP | 2003181757 | A | 7/2003 |
| JP | 2004225514 | A | 8/2004 |
| JP | 2007056642 | A | 3/2007 |
| JP | 2007164366 | A | 6/2007 |
| JP | 2008071263 | A | 3/2008 |
| KR | 20090027027 | A | 3/2009 |
| KR | 20120113573 | A | 10/2012 |
| KR | 20150102282 | A | 9/2015 |
| KR | 20160001079 | A | 1/2016 |
| WO | 20010190859 | A1 | 11/2001 |
| WO | 2007060102 | A1 | 5/2007 |
| WO | 2010107928 | A2 | 9/2010 |
| WO | 2011042703 | A1 | 4/2011 |
| WO | 2011161544 | A2 | 12/2011 |
| WO | 2015054134 | A1 | 4/2015 |
| WO | 2016067028 | A2 | 5/2016 |

OTHER PUBLICATIONS

International Search Report and Written Opinion dated Aug. 31, 2017 in counterpart International Application Serial No. PCT/US2017/038042.
International Search Report and Written Opinion dated Aug. 23, 2017 in counterpart International Application Serial No. PCT/US2017/038025.
International Search Report and Written Opinion dated Sep. 11, 2017 in counterpart International Application Serial No. PCT/US2017/038031.
International Search Report and Written Opinion dated Aug. 25, 2017 in counterpart International Application Serial No. PCT/US2017/038023.
International Search Report and Written Opinion dated Sep. 6, 2017 in counterpart International Application Serial No. PCT/US2017/038044.
International Search Report and Written Opinion dated Sep. 1, 2017 in counterpart International Application Serial No. PCT/US2017/038036.
International Search Report and Written Opinion dated Sep. 11, 2017 in counterpart International Application Serial No. PCT/US2017/038029.
International Search Report and Written Opinion dated Sep. 11, 2017 in counterpart International Application Serial No. PCT/US2017/038040.
Non-Final Office Action issued in counterpart U.S. Appl. No. 15/625,793 dated Jan. 26, 2018.
Non-Final Office Action issued in counterpart U.S. Appl. No. 15/625,807 dated Jan. 11, 2018.
Non-Final Office Action issued in counterpart U.S. Appl. No. 15/625,926 dated Feb. 8, 2018.
Final Office Action issued in U.S. Appl. No. 15/625,793 dated Nov. 1, 2018.
Final Office Action issued in U.S. Appl. No. 15/625,926 dated Nov. 16, 2018.
Final Office Action issued in U.S. Appl. No. 15/625,807 dated Nov. 16, 2018.
Non-Final Office Action issued in U.S. Appl. No. 15/625,775 dated Mar. 6, 2019.
Non-Final Office Action issued in U.S. Appl. No. 15/625,968 dated Apr. 1, 2019.
Non-Final Office Action issued in U.S. Appl. No. 15/625,969 dated Apr. 2, 2019.
Notice of Allowance issued in U.S. Appl. No. 15/625,807 dated Apr. 8, 2019.
Non-Final Office Action issued in U.S. Appl. No. 15/625,851 dated Apr. 19, 2019.
Final Office Action issued in U.S. Appl. No. 15/625,775 dated Jun. 26, 2019.
Final Office Action issued in U.S. Appl. No. 15/625,943 dated Jan. 22, 2019.
Non-Final Office Action issued in U.S. Appl. No. 15/625,925 dated May 30, 2019.
Non-Final Office Action issued in U.S. Appl. No. 15/625,943 dated Jun. 3, 2019.
Notice of Allowance issued in U.S. Appl. No. 15/625,968 dated Oct. 21, 2019.
Notice of Allowance issued in U.S. Appl. No. 15/625,969 dated Oct. 23, 2019.
Final Office Action issued in U.S. Appl. No. 15/625,851 dated Nov. 13, 2019.
Non-Final Office Action issued in U.S. Appl. No. 15/625,888 dated Nov. 18, 2019.
Non-Final Office Action issued in U.S. Appl. No. 15/625,905 dated Nov. 29, 2019.
Final Office Action issued in U.S. Appl. No. 15/625,926 dated Dec. 12, 2019.
Non-Final Office Action issued in U.S. Appl. No. 15/625,853 dated Dec. 27, 2019.
Non-Final Office Action issued in related U.S. Appl. No. 15/625,851 dated Mar. 26, 2020.
Final Office Action issued in related U.S. Appl. No. 15/625,926 dated May 18, 2020.
Final Office Action issued in related U.S. Appl. No. 15/625,905 dated Jun. 9, 2020.
Supplementary European Search Report in related European Application No. 17814236.0 dated Feb. 17, 2020.
Final Office Action issued in related U.S. Appl. No. 15/625,888 dated Jun. 19, 2020.
Extended European Search Report issued in related Application Serial No. 17814245.1 dated Mar. 20, 2020.
Supplementary European Search Report in related European Application No. 17814243 dated Feb. 24, 2020.
Supplementary European Search Report in related European Application No. 178142465 dated Feb. 24, 2020.
Supplementary European Search Report in related European Application No. 17814238 dated Feb. 19, 2020.
Supplementary European Search Report in related European Application No. 17814241 dated Feb. 20, 2020.
Supplementary European Search Report in related European Application No. 17814239 dated Feb. 20, 2020.
Supplementary European Search Report in related European Application No. 17814242 dated Feb. 21, 2020.
Supplementary European Search Report in related European Application No. 17814235.2 dated Feb. 14, 2020.
Notice of Allowance issued in related U.S. Appl. No. 15/625,851 dated Jul. 13, 2020.
Final Office Action issued in related U.S. Appl. No. 15/625,853 dated Jul. 20, 2020.
Non-Final Office Action issued in related U.S. Appl. No. 15/625,943 dated Aug. 3, 2020.
Notice of Allowance issued in related U.S. Appl. No. 15/625,851 dated Aug. 12, 2020.
Non-Final Office Action issued in related U.S. Appl. No. 15/625,905 dated Oct. 6, 2020.
Notice of Allowance issued in related U.S. Appl. No. 15/625,926 dated Oct. 19, 2020.
Communication Pursuant to Article 94(3) EPC in related European Patent Application No. 17814236.0 dated Oct. 28, 2020; 8 pages.

(56) References Cited

OTHER PUBLICATIONS

Communication Pursuant to Article 94(3) EPC in related European Patent Application No. 17814243.6 dated Oct. 28, 2020; 8 pages.
Communication Pursuant to Article 94(3) EPC in related European Patent Application No. 17814246.9 dated Oct. 28, 2020; 9 pages.
Communication Pursuant to Article 94(3) EPC in related European Patent Application No. 17814239.4 dated Oct. 28, 2020; 8 pages.
Communication Pursuant to Article 94(3) EPC in related European Patent Application No. 17814241.0 dated Oct. 28, 2020; 8 pages.
Communication Pursuant to Article 94(3) EPC in related European Patent Application No. 17814242.8 dated Oct. 28, 2020; 9 pages.
Notice of Allowance issued in related U.S. Appl. No. 15/625,905 dated Jan. 29, 2021.
Notice of Allowance issued in related U.S. Appl. No. 15/625,943 dated Feb. 5, 2021.
Non-Final Office Action issued in related U.S. Appl. No. 15/625,888 dated Dec. 24, 2020.
Non-Final Office Action issued in related U.S. Appl. No. 15/625,843 dated Mar. 17, 2021.

\* cited by examiner

ADAPTIVE ALERTNESS TESTING SYSTEM AND METHOD

RELATED APPLICATION

This application claims the benefit of U.S. Provisional Application No. 62/351,665, filed on 17 Jun. 2016, entitled "Impairment Detection Systems and Methods", the contents of which are incorporated herein by reference.

TECHNICAL FIELD

This disclosure relates to detection systems and, more particularly, to impairment detection systems.

BACKGROUND

Accidents in the workplace cost many millions of dollars, hundreds of lives, and damage to the environment every year, wherein the majority of these accidents are caused by human error. As is known, human error has many causes; one of which is impairment (e.g., due to lack of sleep, illness and/or the influence of drugs/alcohol).

In an effort to reduce accidents in the United States, 7.5 million workers in high-risk occupations are required to take random blood and/or urine tests to deter the use of drugs and/or alcohol on the job. However, fatigue, illness and stress are more common causes of impairment than are the effects of drugs or alcohol. Accordingly, accidents continue to occur in large part because workers are impaired by e.g., exhaustion, stress, side-effects from prescription medications or from a combination of these factors.

SUMMARY OF DISCLOSURE

Invention #7

In one implementation, a computer-implemented method is executed on a computing device and includes monitoring one or more environmental variables concerning a client electronic device configured to administer an alertness test to a user. A disrupter is selected for inclusion within the alertness test based, at least in part, upon the one or more environmental variables concerning the client electronic device. The alertness test is administered to the user.

One or more of the following features may be included. Administering the alertness test to the user may include rendering a plurality of objects for use within the alertness test being administered to the user; rendering the disrupter configured to distract the user; and soliciting a response from the user concerning the plurality of objects. The response from the user may be received and a result for the user may be determined based, at least in part, upon the response received from the user. The disrupter may include one or more of: a visual disrupter; an audible disrupter; and a physical disrupter. Monitoring one or more environmental variables concerning a client electronic device may include monitoring a camera included within the client electronic device. Monitoring one or more environmental variables concerning a client electronic device may include monitoring a microphone included within the client electronic device. Monitoring one or more environmental variables concerning a client electronic device may include monitoring a GPS chipset included within the client electronic device.

In another implementation, a computer program product resides on a computer readable medium and has a plurality of instructions stored on it. When executed by a processor, the instructions cause the processor to perform operations including monitoring one or more environmental variables concerning a client electronic device configured to administer an alertness test to a user. A disrupter is selected for inclusion within the alertness test based, at least in part, upon the one or more environmental variables concerning the client electronic device. The alertness test is administered to the user.

One or more of the following features may be included. Administering the alertness test to the user may include rendering a plurality of objects for use within the alertness test being administered to the user; rendering the disrupter configured to distract the user; and soliciting a response from the user concerning the plurality of objects. The response from the user may be received and a result for the user may be determined based, at least in part, upon the response received from the user. The disrupter may include one or more of: a visual disrupter; an audible disrupter; and a physical disrupter. Monitoring one or more environmental variables concerning a client electronic device may include monitoring a camera included within the client electronic device. Monitoring one or more environmental variables concerning a client electronic device may include monitoring a microphone included within the client electronic device. Monitoring one or more environmental variables concerning a client electronic device may include monitoring a GPS chipset included within the client electronic device.

In another implementation, a computing system includes a processor and memory is configured to perform operations including monitoring one or more environmental variables concerning a client electronic device configured to administer an alertness test to a user. A disrupter is selected for inclusion within the alertness test based, at least in part, upon the one or more environmental variables concerning the client electronic device. The alertness test is administered to the user.

One or more of the following features may be included. Administering the alertness test to the user may include rendering a plurality of objects for use within the alertness test being administered to the user; rendering the disrupter configured to distract the user; and soliciting a response from the user concerning the plurality of objects. The response from the user may be received and a result for the user may be determined based, at least in part, upon the response received from the user. The disrupter may include one or more of: a visual disrupter; an audible disrupter; and a physical disrupter. Monitoring one or more environmental variables concerning a client electronic device may include monitoring a camera included within the client electronic device. Monitoring one or more environmental variables concerning a client electronic device may include monitoring a microphone included within the client electronic device. Monitoring one or more environmental variables concerning a client electronic device may include monitoring a GPS chipset included within the client electronic device.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
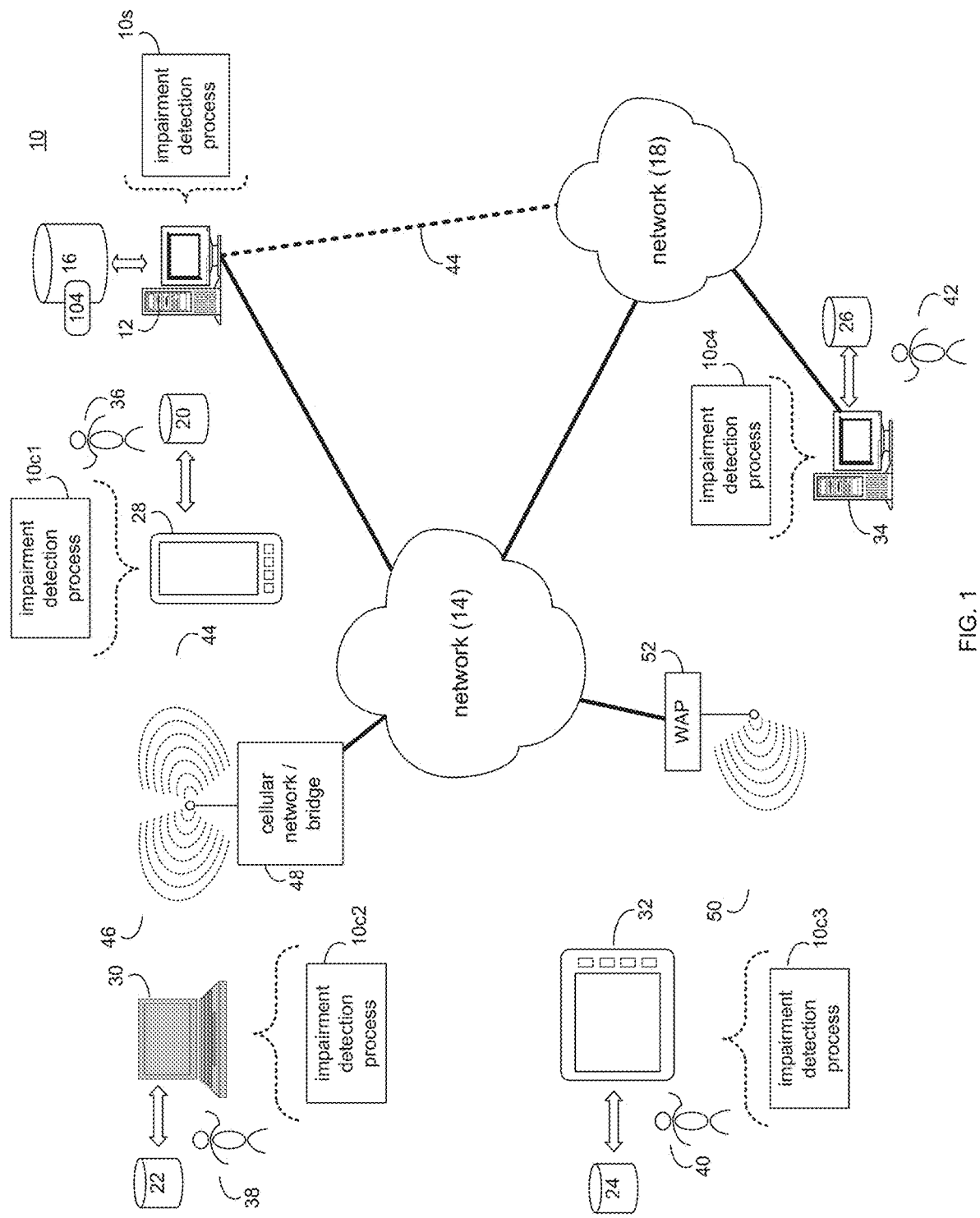
FIG. 1 is a diagrammatic view of a distributed computing network including a computing device that executes an impairment detection process according to an embodiment of the present disclosure.

In FIG. 1, there is shown impairment detection process 10. Impairment detection process 10 may be implemented as a server-side process, a client-side process, or a hybrid server-side/client-side process.

For example, impairment detection process 10 may be implemented as a purely server-side process via impairment detection process 10s. Alternatively, impairment detection process 10 may be implemented as a purely client-side process via one or more of impairment detection process 10c1, impairment detection process 10c2, impairment detection process 10c3, and impairment detection process 10c4. Alternatively still, impairment detection process 10 may be implemented as a hybrid server-side/client-side process via impairment detection process 10s in combination with one or more of impairment detection process 10c1, impairment detection process 10c2, impairment detection process 10c3, and impairment detection process 10c4. Accordingly, impairment detection process 10 as used in this disclosure may include any combination of impairment detection process 10s, impairment detection process 10c1, impairment detection process 10c2, impairment detection process 10c3, and impairment detection process 10c4.

Impairment detection process 10s may be a server application and may reside on and may be executed by computing device 12, which may be connected to network 14 (e.g., the Internet or a local area network). Examples of computing device 12 may include, but are not limited to: a personal computer, a server computer, a series of server computers, a mini computer, a mainframe computer, or a cloud-based computing network.

The instruction sets and subroutines of impairment detection process 10s, which may be stored on storage device 16 coupled to computing device 12, may be executed by one or more processors (not shown) and one or more memory architectures (not shown) included within computing device 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Examples of impairment detection processes 10c1, 10c2, 10c3, 10c4 may include but are not limited to a corporate user interface, a web browser, or a specialized application (e.g., an application running on e.g., the Android™ platform or the iOS™ platform). The instruction sets and subroutines of impairment detection processes 10c1, 10c2, 10c3, 10c4, which may be stored on storage devices 20, 22, 24, 26 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Examples of storage devices 20, 22, 24, 26 may include but are not limited to: hard disk drives; RAID devices; random access memories (RAM); read-only memories (ROM), and all forms of flash memory storage devices.

Examples of client electronic devices 28, 30, 32, 34 may include, but are not limited to: smartphone 28; laptop computer 30; specialty device 32; personal computer 34; a notebook computer (not shown); a server computer (not shown); a dedicated network device (not shown); a tablet computer (not shown), a portion of an area access controller (not shown and configured to allow a user to gain access to a restricted area), a portion of an interlock controller (not shown and configured to allow a user to gain access to a piece of restricted equipment), a portion of a computer access controller (not shown and configured to allow a user to gain access to a restricted computing system) and/or a portion of a timeclock controller (not shown and configured to allow a user to log into work).

Client electronic devices 28, 30, 32, 34 may each execute an operating system, examples of which may include but are not limited to Microsoft Windows™, Android™, iOS™, Linux™, or a custom operating system.

Users 36, 38, 40, 42 may access impairment detection process 10 directly through network 14 or through secondary network 18. Further, impairment detection process 10 may be connected to network 14 through secondary network 18, as illustrated with link line 44.

The various client electronic devices (e.g., client electronic devices 28, 30, 32, 34) may be directly or indirectly coupled to network 14 (or network 18). For example, smartphone 28 and laptop computer 30 are shown wirelessly coupled to network 14 via wireless communication channels 44, 46 (respectively) established between smartphone 28, laptop computer 30 (respectively) and cellular network/bridge 48, which is shown directly coupled to network 14. Further, specialty device 32 is shown wirelessly coupled to network 14 via wireless communication channel 50 established between specialty device 32 and wireless access point (i.e., WAP) 52, which is shown directly coupled to network 14. Additionally, personal computer 34 is shown directly coupled to network 18 via a hardwired network connection.

WAP 52 may be, for example, an IEEE 802.11a, 802.11b, 802.11g, 802.11n, Wi-Fi, and/or Bluetooth device that is capable of establishing wireless communication channel 50 between specialty device 32 and WAP 52. As is known in the art, IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. As is known in the art, Bluetooth is a telecommunications industry specification that allows e.g., mobile phones, computers, and personal digital assistants to be interconnected using a short-range wireless connection.

Figure 2:
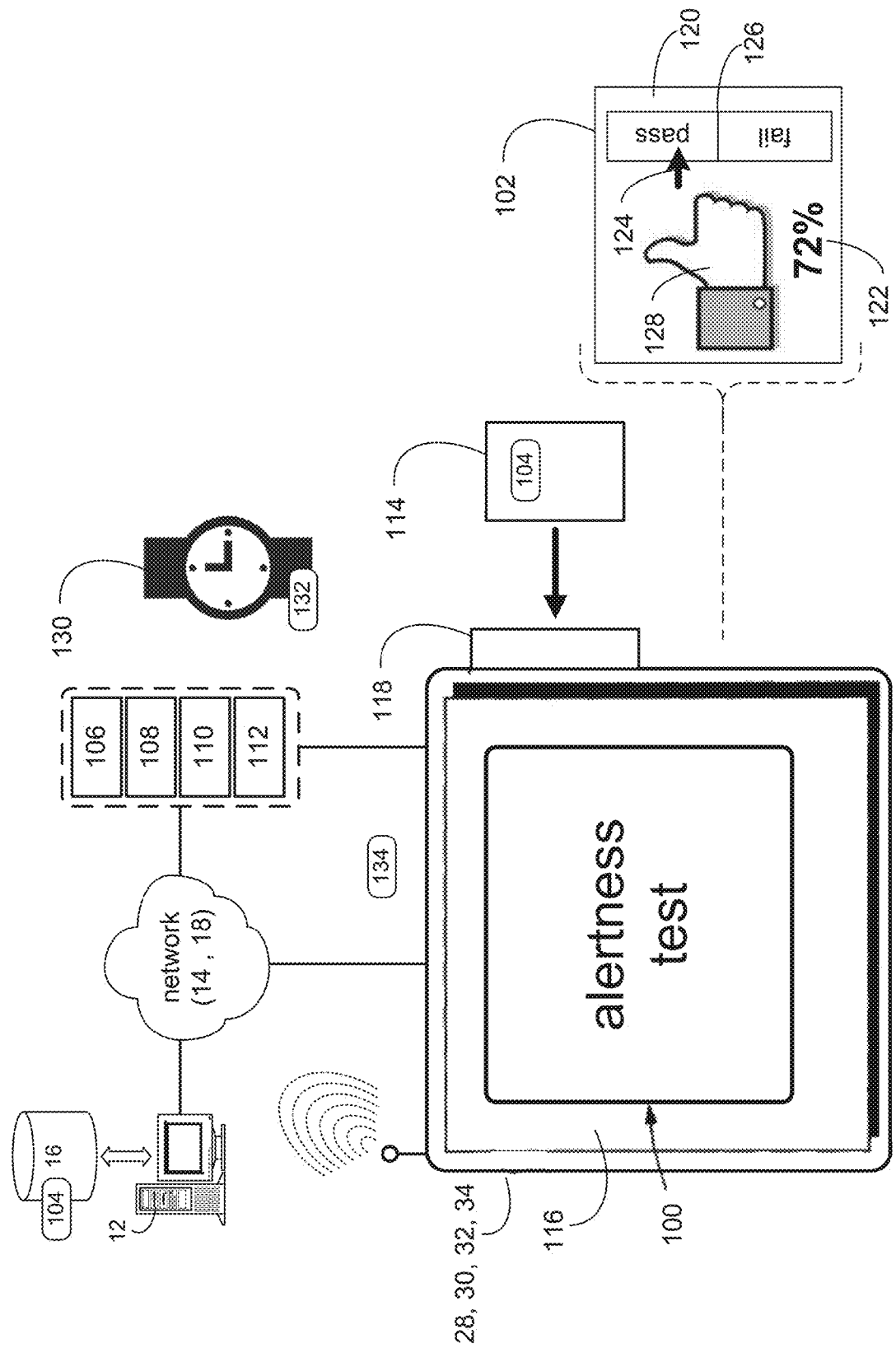
FIG. 2 is a diagrammatic view of a client electronic device executing the impairment detection process of FIG. 1 according to an embodiment of the present disclosure.

Referring to FIG. 2, client electronic device 28, 30, 32, 34 (alone or in combination with computing device 12) may be configured to execute impairment detection process 10 and implement an alertness test (e.g., alertness test 100) to determine a result (e.g., result 102) for the taker (e.g., user 36, 38, 40, 42) of alertness test 100. Result 102 may be indicative of the level of alertness of the taker (e.g., user 36, 38, 40, 42) of alertness test 100. Impairment detection process 10 may then determine if result 102 is sufficient to pass alertness test 100. For example and as will be discussed below in greater detail, result 102 may be required to be at (or proximate) a baseline for the user of alertness test 100 to pass. If the user (e.g., user 36, 38, 40, 42) passes alertness test 100, a passcode (e.g., passcode 104) and other indicia (e.g., actual score, time of test, date of test) may be stored on one or more storage devices.

One example of the one or more storage devices for storing passcode 104 may include but is not limited to a centralized, network accessible storage device (e.g., storage device 16) in implementations in which client electronic devices 28, 30, 32, 34 are hardwired and/or wirelessly-coupled to computing device 12 via network 14 and/or network 18.

Area access controller 106 (i.e., a device for allowing a user to gain access to a restricted area), interlock controller 108 (i.e., a device for allowing a user to gain access to a piece of restricted equipment), computer access controller 110 (i.e., a device for allowing a user to gain access to a restricted computing system) and/or timeclock controller 112 (i.e., a device for allowing a user to log into work) may be hardwired and/or wirelessly-coupled to network 14, network 18 and/or client electronic devices 28, 30, 32, 34 (which may execute impairment detection process 10). Area access controller 106, interlock controller 108, computer access controller 110 and/or timeclock controller 112 may be configured to access/obtain the above-described passcode (e.g., passcode 104) from e.g., storage device 16.

An example of area access controller 106 may include but is not limited to Dortronics of Sag Harbor, N.Y. An example of interlock controller 108 may include but is not limited to products offered by Trimble of Sunnyvale Calif. An example of computer access controller 110 may include but is not limited to products offered by Tyco of Cork, Ireland. An example of timeclock controller 112 may include but is not limited to products offered by Tyco of Cork, Ireland.

Additionally/alternatively, electronic devices 28, 30, 32, 34 (i.e., the devices that execute impairment detection process 10 and implement alertness test 100) may be directly coupled to, wirelessly coupled to, included within and/or a portion of area access controller 106, interlock controller 108, computer access controller 110 and/or a timeclock controller 112.

Another example of the one or more storage devices for storing passcode 104 may include but is not limited to a datacard (e.g., datacard 114) of the user (e.g., user 36, 38, 40, 42), wherein datacard 114 (which e.g., includes passcode 104) may subsequently be utilized to e.g., gain access to a restricted area via area access controller 106, gain access to a piece of restricted equipment via interlock controller 108, gain access to a restricted computing system via computer access controller 110 and/or log into work via timeclock controller 112. Examples of datacard 114 may include but are not limited to an electrical or optical smart card, an electrical or optical identification badge, and an electrical or optical identification bracelet, Centralized Testing with Datacard Storage:

Impairment detection process 10 may be configured to implement centralized testing of alertness test 100. For example, impairment detection process 10 and alertness test 100 may be executed on one or more centralized testing computers (e.g., personal computer 34). During use, employees of a company may insert their datacard 114 into personal computer 34, which may be configured to read data from (and write data to) datacard 114. Personal computer 34 and impairment detection process 10 may be configured to implement an alertness test (e.g., alertness test 100) on personal computer 34. Impairment detection process 10 may determine a result (e.g., result 102) for the test taker (e.g., user 36, 38, 40, 42) and may determine if result 102 is sufficient to pass alertness test 100.

In such a centralized testing configuration, result 102 may be stored on datacard 114 by personal computer 34. If result 102 is sufficient to allow the user (e.g., user 36, 38, 40, 42) to pass alertness test 100, passcode 104 may also be stored on datacard 114. Other indicia may also be stored on datacard 114, examples of which may include but are not limited to: the actual test score, the time of the test, the date of test, a user name, a user identification number, a company name, a security level, a date of hire, a testing level, and a test type.

Specifically and in such a centralized testing configuration, the user (e.g., user 36, 38, 40, 42) may take datacard 114 with them once the administration of alertness test 100 has been completed. Datacard 114 (which may include passcode 104) may then be utilized by the user (e.g., user 36, 38, 40, 42) to gain access to various restricted locations, restricted devices and/or restricted equipment. For example, datacard 114 may be inserted into, accessed and read by:

area access controller 106 (which may be configured to read datacard 114) to determine if the user (e.g., user 36, 38, 40, 42) should be allowed to access a restricted area, such as a control room at a nuclear power plant or a weapon room within a military base;

interlock controller 108 (which may be configured to read datacard 114) to determine if the user (e.g., user 36, 38, 40, 42) should be allowed to gain access a piece of restricted equipment, such as a piece of heavy construction equipment or a piece of aviation equipment;

computer access controller 110 (which may be configured to read datacard 114) to determine if the user (e.g., user 36, 38, 40, 42) should be allowed to access a restricted computing system, certain applications within the restricted computing system and/or certain data within the restricted computing system, such as a computer system that allows access to a company's database or a computer system that that allows access to a weapons control platform; and/or timeclock controller 112 (which may be configured to read datacard 114) to determine if the user (e.g., user

36, 38, 40, 42) should be allowed to log into their job, such as a job as an assembly line worker or a job as a construction worker.

Centralized Testing with Centralized Storage:

As discussed above, impairment detection process 10 may be configured to implement centralized testing of alertness test 100. For example, impairment detection process 10 and alertness test 100 may be executed on one or more centralized testing computers (e.g., personal computer 34), wherein these one or more centralized testing computers (e.g., personal computer 34) may be coupled to a centralized, network accessible storage device (e.g., storage device 16). During use, personal computer 34 and impairment detection process 10 (alone or in combination with computing device 12) may be configured to execute an alertness test (e.g., alertness test 100). Impairment detection process 10 may determine a result (e.g., result 102) for the test taker (e.g., user 36, 38, 40, 42) and may determine if result 102 is sufficient to pass alertness test 100.

In such a centralized testing configuration, result 102 may be stored on a centralized, network accessible storage device (e.g., storage device 16). If result 102 is sufficient to allow the user (e.g., user 36, 38, 40, 42) to pass alertness test 100, passcode 104 and other indicia (such as the actual score, the time of the test, the date of test, etc.) may also be stored on the centralized, network accessible storage device (e.g., storage device 16). In the event that the centralized, network accessible storage device (e.g., storage device 16) is unavailable/offline, the above-described information may be stored locally until the remote storage (e.g., storage device 16) is once again available/online.

Specifically and in such a centralized testing configuration, the centralized, network accessible storage device (e.g., storage device 16) may be accessed so that e.g., result 102, passcode 104 and other indicia may be obtained for the user (e.g., user 36, 38, 40, 42) when the user wishes to gain access to various restricted locations, restricted devices and/or restricted equipment. For example, the user (e.g., user 36, 38, 40, 42) may identify themselves (via e.g., an ID card, an employee number, a fingerprint scan, a retinal scan, etc.) and:

area access controller 106 (which may be coupled to storage device 16) may determine if the user (e.g., user 36, 38, 40, 42) should be allowed to access a restricted area, such as a control room at a nuclear power plant or a weapon room within a military base;

interlock controller 108 (which may be coupled to storage device 16) may determine if the user (e.g., user 36, 38, 40, 42) should be allowed to gain access a piece of restricted equipment, such as a piece of heavy construction equipment or a piece of aviation equipment;

computer access controller 110 (which may be coupled to storage device 16) may determine if the user (e.g., user 36, 38, 40, 42) should be allowed to access a restricted computing system, certain applications within the restricted computing system and/or certain data within the restricted computing system, such as a computer system that allows access to a company's database or a computer system that allows access to a weapons control system; and/or timeclock controller 112 (which may be coupled to storage device 16) may determine if the user (e.g., user 36, 38, 40, 42) should be allowed to log into their job, such as a job as an assembly line worker or a job as a construction worker.

Localized Testing with Datacard Storage:

Impairment detection process 10 may be configured to implement localized testing of alertness test 100. As discussed above, electronic devices 28, 30, 32, 34 (i.e., the devices that implement alertness test 100) may be directly coupled to, wirelessly coupled to, included within and/or a portion of area access controller 106, interlock controller 108, computer access controller 110 and/or a timeclock controller 112.

Accordingly, in addition to allowing a user to gain access to a restricted area, area access controller 106 may also be configured to execute impairment detection process 10 and implement alertness test 100. And in addition to allowing a user to gain access to a piece of restricted equipment, interlock controller 108 may also be configured to execute impairment detection process 10 and alertness test 100. Further, in addition to allowing a user to gain access to a restricted computing system, computer access controller 110 may also be configured to execute impairment detection process 10 and implement alertness test 100. Further still, in addition to allowing a user to log into work, timeclock controller 112 may also be configured to execute impairment detection process 10 and implement alertness test 100.

Accordingly and in such a configuration, a separate and discrete alertness test 100 may need to be implemented each time the user (e.g., user 36, 38, 40, 42) wishes to gain access to various restricted locations, restricted devices and/or restricted equipment. So if the user (e.g., user 36, 38, 40, 42) wishes to gain access to a control room, area access controller 106 may be configured to execute impairment detection process 10 and implement alertness test 100 for the user (e.g., user 36, 38, 40, 42) to determine if the user may enter the control room. If the user (e.g., user 36, 38, 40, 42) leaves the control room and then wishes to utilize a bulldozer, interlock controller 108 may be configured to execute impairment detection process 10 and implement alertness test 100 for the user (e.g., user 36, 38, 40, 42) to determine if the user may utilize the bulldozer. If the user (e.g., user 36, 38, 40, 42) has completed using the bulldozer and then wishes to access the payroll system for the company with which they are employed, timeclock controller 112 may be configured to execute impairment detection process 10 and implement alertness test 100 for the user (e.g., user 36, 38, 40, 42) to determine if the user may access the payroll system for the company with which they are employed.

When executing the above-described impairment detection process 10 and implementing alertness test 100, employees of a company may insert their datacard 114 into e.g., the above-described area access controller 106, interlock controller 108, computer access controller 110 and/or timeclock controller 112, each of which may be configured to read data from (and write data to) datacard 114. In such an implementation, area access controller 106, interlock controller 108, computer access controller 110 and/or timeclock controller 112 may then implement alertness test 100. Impairment detection process 10 may determine a result (e.g., result 102) for the test taker (e.g., user 36, 38, 40, 42) and may determine if result 102 is sufficient to pass alertness test 100, wherein result 102 may be stored on datacard 114. If result 102 is sufficient to allow the user (e.g., user 36, 38, 40, 42) to pass alertness test 100, passcode 104 and other indicia (such as the actual score, the time of the test, the date of test, etc.) may also be stored on datacard 114.

Further and in such a localized testing configuration, the user (e.g., user 36, 38, 40, 42) may take datacard 114 with them once the administration of alertness test 100 has been completed, so that datacard 114 may be utilized when additional testing is required to determine if the user (e.g., user 36, 38, 40, 42) should be allowed to gain access to other restricted locations, restricted devices and/or restricted equipment. Additionally, datacard 114 may be configured to permanently (or semi-permanently) store result 102, passcode 104 and any other indicia.

Localized Testing with Centralized Storage:

As discussed above, impairment detection process 10 may be configured to implement localized testing of alertness test 100. As discussed above, in addition to allowing a user to gain access to a restricted area, area access controller 106 may also be configured to execute impairment detection process 10 and implement alertness test 100. And in addition to allowing a user to gain access to a piece of restricted equipment, interlock controller 108 may also be configured to execute impairment detection process 10 and implement alertness test 100. Further, in addition to allowing a user to gain access to a restricted computing system, computer access controller 110 may also be configured to execute impairment detection process 10 and implement alertness test 100. Further still, in addition to allowing a user to log into work, timeclock controller 112 may also be configured to execute impairment detection process 10 and implement alertness test 100.

Further and as discussed above, a separate and discrete alertness test 100 may need to be implemented each time the user (e.g., user 36, 38, 40, 42) wishes to gain access to various restricted locations, restricted devices and/or restricted equipment (e.g., a first test when the user wishes to gain access to a control room, a second test when the user wishes to utilize a bulldozer, and a third test when the user wishes to access the payroll system for the company with which they are employed).

In such an implementation, area access controller 106, interlock controller 108, computer access controller 110 and timeclock controller 112 may be coupled to a centralized, network accessible storage device (e.g., storage device 16). Further, area access controller 106, interlock controller 108, computer access controller 110 and/or timeclock controller 112 may execute alertness test 100 and impairment detection process 10 may determine a result (e.g., result 102) for the test taker (e.g., user 36, 38, 40, 42) and may determine if result 102 is sufficient to pass alertness test 100. Result 102 may be stored on the centralized, network accessible storage device (e.g., storage device 16). If result 102 is sufficient to allow the user (e.g., user 36, 38, 40, 42) to pass alertness test 100, passcode 104 and other indicia (such as the actual score, the time of the test, the date of test, etc.) may also be stored on the centralized, network accessible storage device (e.g., storage device 16). Additionally, the centralized, network accessible storage device (e.g., storage device 16) may be configured to permanently (or semi-permanently) store result 102, passcode 104 and any other indicia. In the event that the centralized, network accessible storage device (e.g., storage device 16) is unavailable/offline, the above-described information may be stored locally until the remote storage (e.g., storage device 16) is once again available/online.

General Implementations:

Impairment detection process 10 may implement alertness test 100 as a video-based/movement-based test. Alertness test 100 may be administered to the user (e.g., user 36, 38, 40, 42) in various configurations, wherein some configurations may take longer to complete and other configurations may be completed comparatively quickly (e.g., in one minute or less). Additionally and if the user (e.g., user 36, 38, 40, 42) performs particularly well on a given day, impairment detection process 10 may be configured to provide the user (e.g., user 36, 38, 40, 42) with a passing score after a shortened test period (thus allowing the user to complete alertness test 100 early).

Impairment detection process 10 may render the test result (e.g., result 102) of the user (e.g., user 36, 38, 40, 42) on a display screen (e.g., display screen 116) of client electronic device 28, 30, 32, 34. Result 102 may then be saved on a centralized, network accessible storage device (e.g., storage device 16) or datacard 114. Accordingly, client electronic devices 28, 30, 32, 34 may be configured to be coupled to storage device 16 and/or configured to be coupled to card reader 118.

In one implementation, impairment detection process 10 may be configured to allow the user (e.g., user 36, 38, 40, 42) to immediately retake alertness test 100 in the event that the user (e.g., user 36, 38, 40, 42) fails alertness test 100. In other implementations, impairment detection process 10 may be configured to prevent the user (e.g., user 36, 38, 40, 42) from immediately retaking alertness test 100 in the event that the user (e.g., user 36, 38, 40, 42) fails alertness test 100.

In configurations that utilize a datacard, when initially inserting datacard 114 into card reader 118 of client electronic device 28, 30, 32, 34, impairment detection process 10 may determine whether datacard 114 is invalid/unreadable/malfunctioning. In the event that datacard 114 is invalid/unreadable/malfunctioning, impairment detection process 10 may render an error message on display screen 116.

In configurations that utilize centralized storage, the user (e.g., user 36, 38, 40, 42) may identify themselves (via e.g., an ID card, an employee number, a fingerprint scan, a retinal scan, etc.) on client electronic device 28, 30, 32, 34 and impairment detection process 10 may determine that storage device 16 is accessible. In the event that storage device 16 is not accessible, impairment detection process 10 may render an error message on display screen 116.

Assuming that datacard 114 is valid and readable and/or storage device 16 is accessible; upon completion of alertness test 100, impairment detection process 10 may be configured to render on display screen 116 an alertness gauge (e.g., alertness gauge 120) that may be configured to graphically display a score of the user (e.g., user 36, 38, 40, 42) relative to the baseline (e.g., a passing grade) for alertness test 100.

For example, impairment detection process 10 and alertness gauge 120 may be configured to textually render a numeric score 122 of the user (e.g., user 36, 38, 40, 42) on display screen 116. Additionally/alternatively, impairment detection process 10 and alertness gauge 120 may be configured to graphically render a score (e.g., arrow 124) of the user (e.g., user 36, 38, 40, 42) relative to an absolute pass/fail line (e.g., pass/fail line 126) that defines the passing range of scores and the failing range of scores. Accordingly, all feedback and indicators rendered by impairment detection process 10 may be provided in various forms, examples of which may include but are not limited to e.g., text-based indicia (e.g., numeric score 122), graphical indicia (e.g., arrow 124) and/or graphical symbols (e.g., thumbs up symbol 128 or a thumbs down symbol (not shown)).

Alertness Test Implementations:

As will be discussed below in greater detail, alertness test 100 may be implemented in various fashions that require the user (e.g., user 36, 38, 40, 42) to examine objects to determine whether the displayed objects match.

Figure 3A:
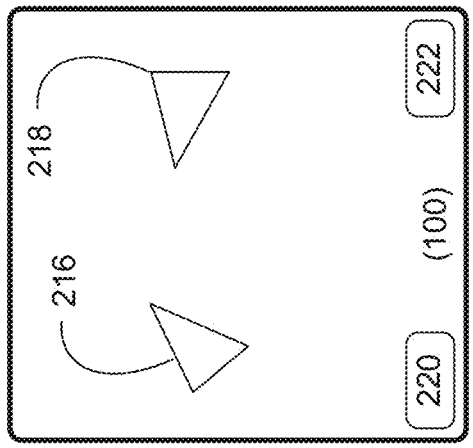
FIGS. 3A-3F are a diagrammatic views of display screens rendered by the impairment detection process of FIG. 1 according to an embodiment of the present disclosure.
Figure 4:
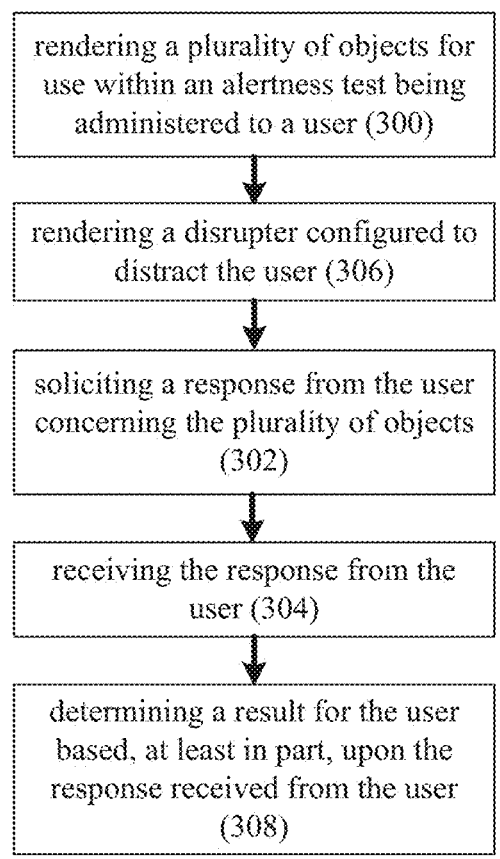
FIG. 4 is a flowchart of one embodiment of the impairment detection process of FIG. 1 according to an embodiment of the present disclosure.

The particular manner in which alertness test 100 is implemented may vary depending upon e.g., the type of processor/memory included within client electronic device 28, 30, 32, 34, the type of display included within client electronic device 28, 30, 32, 34, and the type of network connection available to client electronic device 28, 30, 32, 34. Examples of the types of alertness tests (e.g., alertness test 100) that impairment detection process 10 may implement may include but are not limited to:

- Referring also to FIG. 3A and FIG. 4, there is shown an implementation of alertness test 100 that includes a pair of static objects (e.g., objects 200, 202) that are rendered 300 by impairment detection process 10, wherein the pair of static objects (e.g., objects 200, 202) may or may not be different. In such an implementation, impairment detection process 10 may solicit 302 a response from the user (e.g., user 36, 38, 40, 42) and the user may be required to indicate whether the pair of static objects (e.g., objects 200, 202) are identical by pressing YES buttons 204 or NO button 206. This response may be received 304 by impairment detection process 10 from the user (e.g., user 36, 38, 40, 42). Examples of YES buttons 204 or NO button 206 may include but are not limited to physical (i.e., mechanical) buttons and soft buttons (selectable via e.g., a touchscreen, a stylus or a mouse).

Figure 3B:
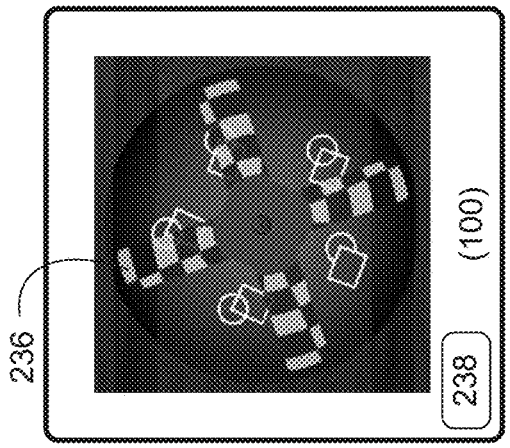

- Referring also to FIG. 3B and FIG. 4, there is shown an implementation of alertness test 300 that includes three or more static objects (e.g., objects 208, 210, 212) that are rendered 300 by impairment detection process 10, wherein one of the three or more static objects (e.g., objects 208, 210, 212) may be different. In such an implementation, impairment detection process 10 may solicit 302 a response from the user (e.g., user 36, 38, 40, 42) and the user may be required to identify the static object that is different by selecting it (e.g., via a touch command, a stylus or a mouse click) or the user (e.g., user 36, 38, 40, 42) may select "They're All the Same" button 214 (e.g., via a touch command, a stylus or a mouse click). This response may be received 304 by impairment detection process 10 from the user (e.g., user 36, 38, 40, 42).

Figure 3C:
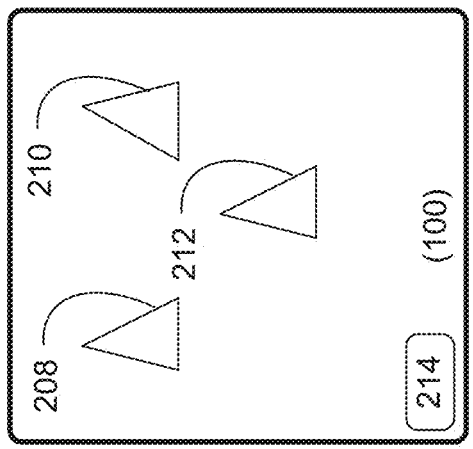

- Referring also to FIG. 3C and FIG. 4, there is shown an implementation of alertness test 300 that includes a pair of moving objects (e.g., objects 216, 218) that are rendered 300 by impairment detection process 10, wherein the pair of moving objects (e.g., objects 216, 218) may or may not be different. This pair of moving objects (e.g., objects 216, 218) may be e.g., rotating with respect to themselves, rotating with respect to each other, sliding around display screen 116, or a combination of thereof. In such an implementation, impairment detection process 10 may solicit 302 a response from the user (e.g., user 36, 38, 40, 42) and the user may be required to indicate whether the pair of moving objects (e.g., objects 216, 218) are identical by pressing YES buttons 220 or NO button 222. This response may be received 304 by impairment detection process 10 from the user (e.g., user 36, 38, 40, 42). Examples of YES buttons 220 or NO button 222 may include but are not limited to physical (i.e., mechanical) buttons and soft buttons (selectable via e.g., a touchscreen, a stylus or a mouse).

Figure 3D:
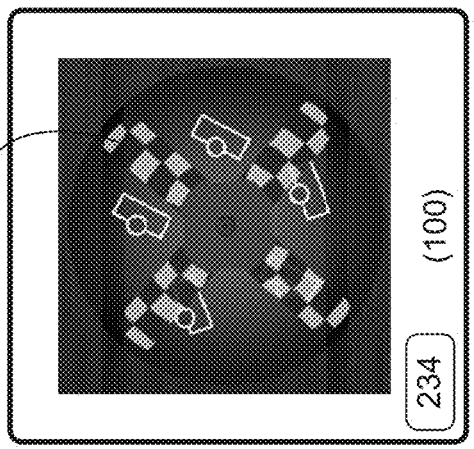

- Referring also to FIG. 3D and FIG. 4, there is shown an implementation of alertness test 300 that includes three or more moving objects (e.g., objects 224, 226, 228) that are rendered 300 by impairment detection process 10, wherein one of the three or more moving objects (e.g., objects 224, 226, 228) may be different. These moving objects (e.g., objects 224, 226, 228) may be e.g., rotating with respect to themselves, rotating with respect to each other, sliding around display screen 116, or a combination of thereof. In such an implementation, impairment detection process 10 may solicit 302 a response from the user (e.g., user 36, 38, 40, 42) and the user may be required to identify the moving object that is different by selecting it (e.g., via a touch command, a stylus or a mouse click) or the user (e.g., user 36, 38, 40, 42) may select "They're All the Same" button 230 (e.g., via a touch command, a stylus or a mouse click). This response may be received 304 by impairment detection process 10 from the user (e.g., user 36, 38, 40, 42).

Figure 3E:
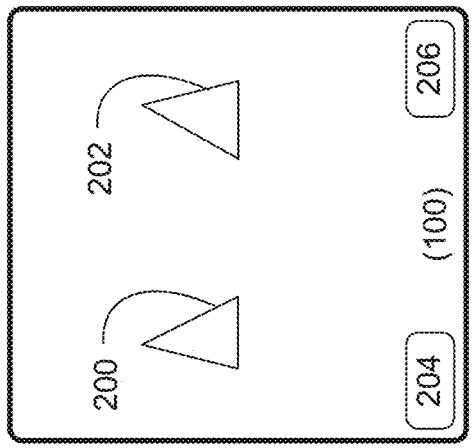

- Referring also to FIG. 3E and FIG. 4, there is shown an implementation of alertness test 300 that includes a disrupter (e.g., disrupter 232) rendered 306 by impairment detection process 10. In this particular embodiment, disrupter 232 may be configured to rotate. Additionally and in this implementation, alertness test 100 is shown to include five objects that may be configured to remain static, rotate with respect to themselves, rotate with respect to each other, slide around display screen 116, or any combination thereof. In this particular implementation, disrupter 232 may be configured to distract the user (e.g., user 36, 38, 40, 42). For example, disrupter 232 may be configured to change color, change shape, change rotational direction, change rotational speed, etc. Accordingly and in this implementation, disrupter 232 may temporarily obscure one or more of the five objects included within this embodiment of alertness test 100. In such an implementation, impairment detection process 10 may solicit 302 a response from the user (e.g., user 36, 38, 40, 42) and the user may be required to identify the object that is different by selecting it (e.g., via a touch command, a stylus or a mouse click) or the user (e.g., user 36, 38, 40, 42) may select "They're All the Same" button 234 (e.g., via a touch command, a stylus or a mouse click). This response may be received 304 by impairment detection process 10 from the user (e.g., user 36, 38, 40, 42).

Figure 3F:
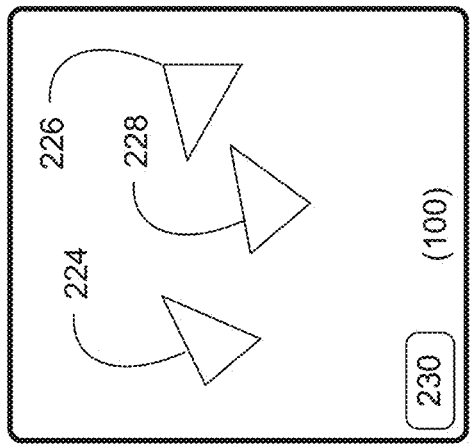

- Referring also to FIG. 3F and FIG. 4, there is shown another implementation of alertness test 300 that includes a disrupter (e.g., disrupter 236) rendered 306 by impairment detection process 10. In this particular embodiment, disrupter 236 may be configured to rotate. Additionally and in this implementation, alertness test 100 is shown to include five objects that may be configured to remain static, rotate with respect to themselves, rotate with respect to each other, slide around display screen 116, or any combination thereof. In this particular implementation, disrupter 236 may be configured to distract the user (e.g., user 36, 38, 40, 42). For example, disrupter 236 may be configured to change color, change shape, change rotational direction, change rotational speed, etc. Accordingly and in this implementation, disrupter 236 may temporarily obscure one or more of the five objects included within this embodiment of alertness test 100. In such an implementation, impairment detection process 10 may solicit 302 a response from the user (e.g., user 36, 38, 40, 42) and the user may be required to identify the object that is different by selecting it (e.g., via a touch command, a stylus or a mouse click) or the user (e.g., user 36, 38, 40, 42) may select "They're All the Same" button 238 (e.g., via a touch command, a stylus or a mouse click). This response may be received 304 by impairment detection process 10 from the user (e.g., user 36, 38, 40, 42).

While the above-described disrupters (e.g., disrupters 232, 236) are shown as being a propeller, this is for illustrative purposes only and is not intended to be a limitation of this disclosure. For example, these disrupters may also include other visually-disruptive effects, such as any combination of areas of changing background color of display screen 116, areas of moving visual distortion of display screen 116, areas of blanking/saturating/washing of display screen 116, areas of variable and/or user-definable transparency, and the use of animated characters/images/overlays on display screen 116. Additionally/alternatively, these disrupters may also include audibly-disruptive components, such as any combination of disrupting sounds (e.g., ring tones, clicking sounds, screaming, crying), disrupting music, disrupting conversations/language/spoken words, and disrupting noise. Additionally/alternatively, these disrupters may also include physically-disruptive components, such as any combination of vibrations/haptic feedback. Additionally/alternatively, these disrupters may also include temporally-disruptive components, such as the rendering of a first object, followed by the blanking of display screen 116 to introduce a delay for a defined period of time, followed by the rendering of a plurality of objects from which the user needs to choose the one object that matches the previously-rendered object. Accordingly, a disruptor (e.g., disrupters 232, 236) may be any combination of visually-disruptive elements, audibly-disruptive elements, physically-disruptive elements, and/or temporally-disruptive elements that is designed to confuse/distract/disorient/annoy the user (e.g., user 36, 38, 40, 42) and make it more difficult for them to focus on achieving a desired task (e.g., such as the examination of objects).

The various buttons described above (e.g., buttons 204, 206, 214, 220, 222, 230, 234, 238) may be spaced far enough apart to allow the users (e.g., user 36, 38, 40, 42) to use either one or both hands to respond, wherein buttons 204, 206, 214, 220, 222, 230, 234, 238 may be large enough (or configured) to be used while e.g., wearing gloves.

The enclosure of client electronic device 28, 30, 32, 34 may be configured in various manners depending upon the particular implementation of the device. For example, if the client electronic device (e.g., client electronic device 28, 30, 32, 34) is a specialty device (e.g., specialty device 32), the enclosure may be wall-mounted. Alternatively, one or more of client electronic device 28, 30, 32, 34 may be positioned on a piece of furniture, mounted within a vehicle, mounted within a piece of construction equipment, mounted within a piece of aviation equipment, mounted to a piece of assembly line equipment, mounted to a piece of mechanical equipment, mounted on an access door, mounted on an access panel, or attached to a computing device, for example.

Operation of Alertness Test:

The following discussion concerns the general operation of impairment detection process 10 and the implementation of alertness test 100. The identity of the user (e.g., user 36, 38, 40, 42) and (if available) any baseline performance data may be read by impairment detection process 10 from e.g., centralized, network accessible storage device (e.g., storage device 16) or datacard 114 (when inserted into datacard reader 118). An example of a baseline for a user (e.g., user 36, 38, 40, 42) may include but is not limited to a measure of the normal daily level of alertness and mental fitness of the user. For example, a baseline for a user (e.g., user 36, 38, 40, 42) may be the average of the last ten, twenty or fifty test results (e.g., result 102) determined 308 by impairment detection process 10. Naturally, as a user performs additional testing, this baseline may change as newer test results determined 308 by impairment detection process 10 may be added to the baseline calculation and older test results may be removed from the baseline calculation.

When a baseline is being established for a user (e.g., user 36, 38, 40, 42), data may be read from and/or written to e.g., centralized, network accessible storage device (e.g., storage device 16) or datacard 114. Once the baseline is established, this baseline may be accessed at the start of each test (e.g., alertness test 100) and may be used for comparison to the test results (e.g., result 102) determined 308 by impairment detection process 100 for the user (e.g., user 36, 38, 40, 42) to determine whether a user is alert enough to performs a specific task.

Alternatively and in some situations, the use of a baseline may not be practical/possible when determining if someone has the requisite level of alertness to perform a task. For example, a roadside alertness test performed at a police checkpoint may not allow the use of a baseline, as the people being tested are random strangers and, therefore, there is no testing history from which a baseline may be calculated. Accordingly and in such situations, a simple pass/fail determine may be made by requiring the user (e.g., user 36, 38, 40, 42) to get 70% of the questions correct.

As discussed above, once the administration of alertness test 100 has been completed and if the user (e.g., user 36, 38, 40, 42) passes alertness test 100, pass code 104 and other indicia (e.g., actual score, time of test, date of test) may be stored on one or more storage devices (e.g., storage device 16 and/or datacard 114). Conversely, if the user (e.g., user 36, 38, 40, 42) fails alertness test 100, impairment detection process 10 may write a fail code (or no code) to the one or more storage devices (e.g., storage device 16 and/or datacard 114).

When data (e.g., a pass code, a fail code or other indicia) is written to the storage device (e.g., storage device 16 or datacard 114), the data may be stored permanently or temporarily. For example and when permanently stored, the data may be maintained indefinitely until purposefully deleted. Alternatively and when temporarily stored, the data may be maintained for a defined period of time (e.g., a minute, an hour, a day, a week) and then automatically deleted.

Impairment detection process 10 may be configured to perform a fundamental screening and baselining of users via alertness test 100 to identify those users who are significantly below, at, or significantly above their own normal daily level of alertness and mental fitness (i.e., their baseline). Additionally, alertness test 100 may be configured to test for broad-based, generalized alertness, to test for specific types of alertness, and/or to test for alertness concerning a specific task. Additionally, impairment detection process 10 may be configured to establish a baseline for each type of task that a user may perform, wherein these multiple baselines may be configured to be building blocks/prerequisites of each other, or standalone tests/baselines. For example, the same construction work may be required to have a higher level of alertness when operating a crane then when driving a pickup truck.

Generally, impairment detection process 10 and alertness test 100 may be configured to determine a user's level of visual perception, information processing, focused attention, decision-making, and eye-hand coordination, wherein these levels may indicate the level of general alertness and mental fitness for a user. Accordingly, the failing of alertness test 100 may indicates that the user has a level of alertness that is reduced to a level below a predefined percentage of their normal baseline.

Short Term Memory Testing:

As discussed above, impairment detection process 10 may be configured to administer various implementations of alertness test 100, wherein one or more objects may be rendered and a response may be solicited from a user (e.g., user 36, 38, 40, 42) concerning the rendered objects. These various implementations of alertness test 100 may be configured to accomplish many different tasks. For example, impairment detection process 10 may administer an implementation of alertness test 100 that is configured to test short term memory.

Figure 5:
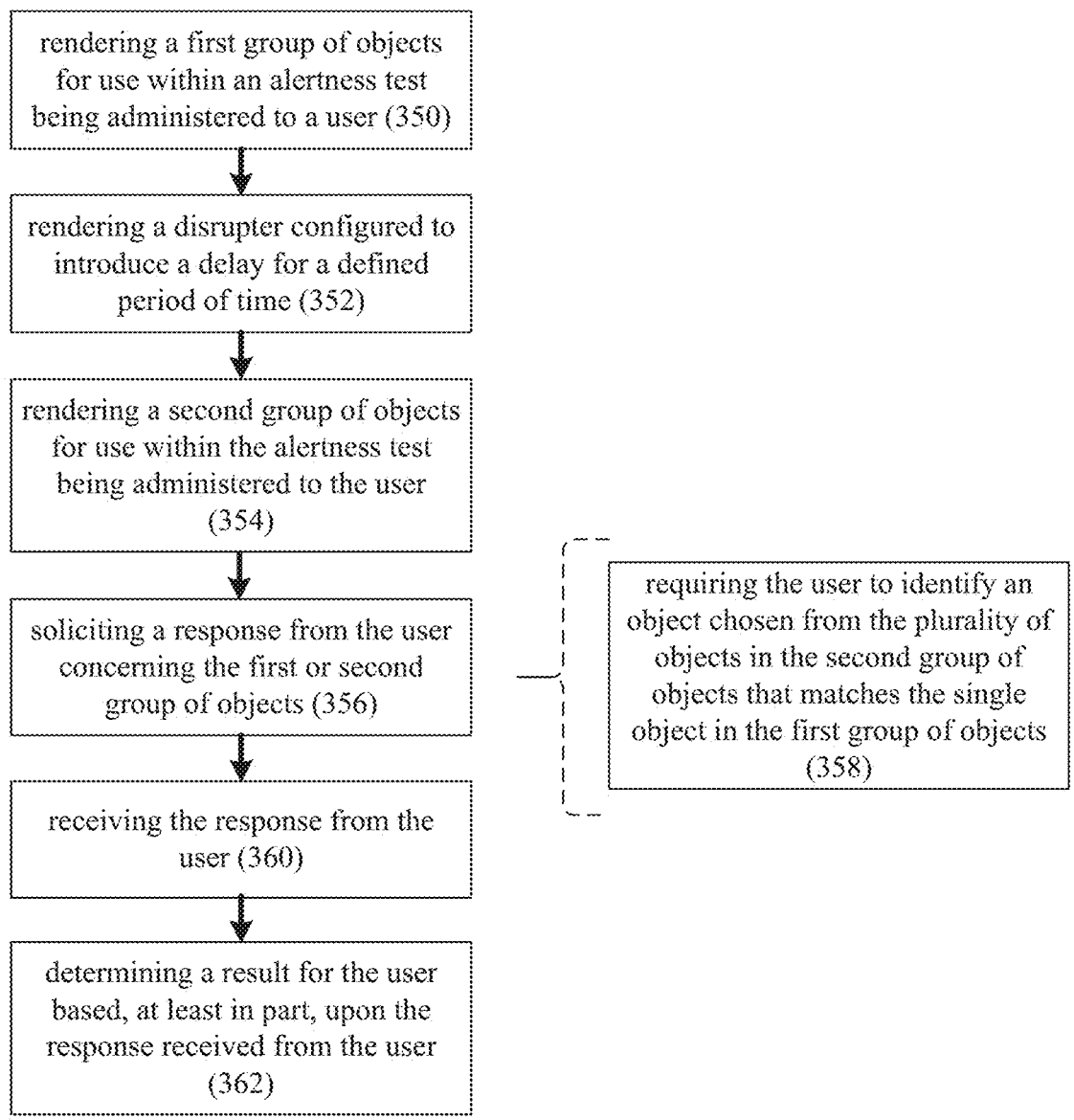
FIG. 5 is a flowchart of another embodiment of the impairment detection process of FIG. 1 according to an embodiment of the present disclosure.

Referring also to FIG. 5, impairment detection process 10 may render 350 a first group of objects for use within alertness test 100 being administered to a user (e.g., user 36, 38, 40, 42). The first group of objects may include a single object. For example, impairment detection process 10 may render 350 a single object on display screen 116 (in a fashion similar to the objects shown in FIGS. 3A-3F).

Impairment detection process 10 may then render 352 a disrupter configured to introduce a delay for a defined period of time. One example of this disrupter may include but is not limited to blanking display screen 116 associated with alertness test 100 for the defined period of time. Examples of this defined period of time may vary from seconds to hours depending upon the implementation of alertness test 100, and, during this defined period of time, the shape previously rendered 350 is not shown.

Another example of this disrupter may include any of the disrupters defined above, such as any combination of visually-disruptive elements, audibly-disruptive elements, physically-disruptive elements, and/or temporally-disruptive elements that is designed to confuse/distract/disorient/annoy the user (e.g., user 36, 38, 40, 42) and make it more difficult for them to focus on achieving a desired task.

Impairment detection process 10 may then render 354 a second group of objects for use within alertness test 100 being administered to the user (e.g., user 36, 38, 40, 42). This second group of objects may include a plurality of objects. For example, impairment detection process 10 may render 354 a group of e.g., three to six objects on display screen 116 (in a fashion similar to the objects shown in FIGS. 3A-3F).

Impairment detection process 10 may then solicit 356 a response from the user (e.g., user 36, 38, 40, 42) concerning the first group of objects rendered 350 or the second group of objects rendered 354. Soliciting 356 a response from the user (e.g., user 36, 38, 40, 42) may include requiring 358 the user to identify an object (chosen from the plurality of objects in the second group of objects) that matches the single object in the first group of objects. For example, the user (e.g., user 36, 38, 40, 42) may be required to identify the matching object by selecting it (e.g., via a touch command, a stylus or a mouse click).

This response may be received 360 by impairment detection process 10 from the user (e.g., user 36, 38, 40, 42) and impairment detection process 10 may then determine 362 a result for the user (e.g., user 36, 38, 40, 42) based, at least in part, upon the response received from the user (in a fashion similar to that described above).

Adaptive Alertness Testing:

As discussed above, impairment detection process 10 may be configured to administer various implementations of alertness test 100. Further and when administering alertness test 10, impairment detection process 10 may: render a plurality of objects for use within alertness test 100 being administered to a user (e.g., user 36, 38, 40, 42); render a disrupter (e.g., disrupter 232, 236) configured to distract the user; solicit a response from the user concerning the plurality of objects; receive the response from the user; and determine a result for the user based (at least in part) upon the response received from the user. Further, alertness test 100 (or portions thereof, such as the above-described disrupters) may be adaptive in nature and may be adjustable based upon environmental variables concerning the client electronic device administering alertness test 100 or the user taking administrative test 100. Examples of such environmental variables may include but are not limited to: local time, elapsed time, location of the user/device, sound proximate the user/device, lighting conditions proximate the user/device, temperature proximate the user/device, humidity proximate the user/device, the presence/concentration of gas(es) proximate the user/device, etc.

Figure 6:
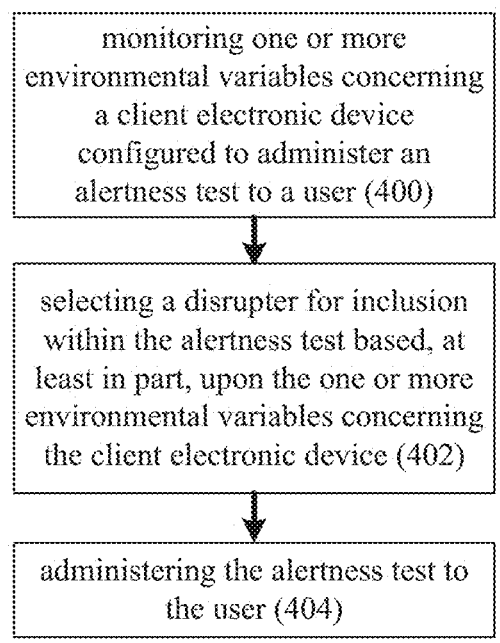
FIG. 6 is a flowchart of another embodiment of the impairment detection process of FIG. 1 according to an embodiment of the present disclosure.

Specifically and referring also to FIG. 6, impairment detection process 10 may monitor 400 one or more environmental variables concerning a client electronic device (e.g., client electronic device 28, 30, 32, 34) configured to administer alertness test 100 to a user (e.g., user 36, 38, 40, 42). Impairment detection process 10 may select 402 a disrupter for inclusion within alertness test 100 based, at least in part, upon the environmental variables concerning the client electronic device (e.g., client electronic device 28, 30, 32, 34). Impairment detection process 10 may then administer 404 alertness test 100 to the user (e.g., user 36, 38, 40, 42), wherein the alertness test administered includes the selected disrupter.

Accordingly and when monitoring 400 environmental variables concerning the client electronic device, impairment detection process 10 may monitor e.g., the camera, the microphone, and/or the GPS chipset of client electronic device 28, 30, 32, 34 and may select 402 a disrupter for inclusion within alertness test 100 based, at least in part, upon the environmental variables monitored 400 concerning the client electronic device (e.g., client electronic device 28, 30, 32, 34).

For example, impairment detection process 10 may monitor 400 the microphone included within the client electronic device and, when the user (e.g., user 36, 38, 40, 42) is in a noisy environment, impairment detection process 10 may select 402 a visual disrupter. Conversely and when the user (e.g., user 36, 38, 40, 42) is in a quiet environment, impairment detection process 10 may select 402 an audible disrupter. Impairment detection process 10 may then administer 404 alertness test 100 to the user.

Additionally, impairment detection process 10 may monitor 400 the camera included within the client electronic device and, when the user (e.g., user 36, 38, 40, 42) is in a dark environment, impairment detection process 10 may select 402 a bright visual disrupter. Impairment detection process 10 may then administer 404 alertness test 100 to the user.

Further, impairment detection process 10 may monitor 400 the GPS chipset included within the client electronic device to determine the location of the client electronic device. And when using disrupting conversations/language/spoken words, impairment detection process 10 may determine the native language of the location and may select 402 a disrupter (that includes conversations/language/spoken words) in the native language (to prevent the disrupting conversations/language/spoken words from being mentallydismissed as background noise). Impairment detection process 10 may then administer 404 alertness test 100 to the user.

Figure 7:
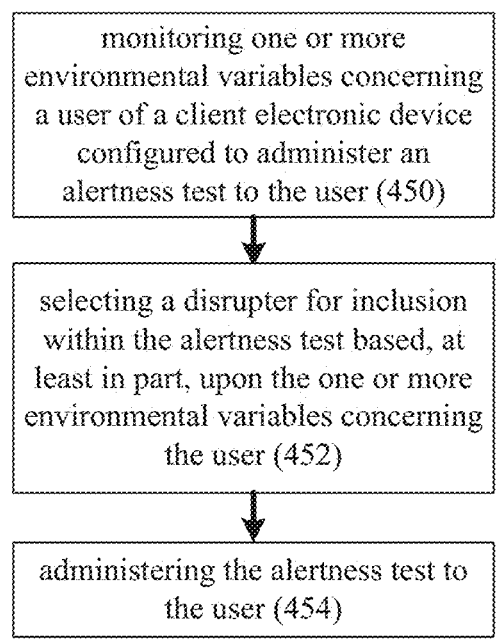
FIG. 7 is a flowchart of another embodiment of the impairment detection process of FIG. 1 according to an embodiment of the present disclosure.

Further and referring also to FIG. 7, impairment detection process 10 may monitor 450 one or more environmental variables concerning a user (e.g., user 36, 38, 40, 42) of a client electronic device (e.g., client electronic device 28, 30, 32, 34) configured to administer alertness test 100. Impairment detection process 10 may select 452 a disrupter for inclusion within alertness test 100 based, at least in part, upon the environmental variables concerning the user. Impairment detection process 10 may then administer 454 alertness test 100 to the user (e.g., user 36, 38, 40, 42), wherein the alertness test administered includes the selected disrupter.

Accordingly and when monitoring 450 environmental variables concerning the user, impairment detection process 10 may monitor e.g., the clock, the camera and/or the GPS chipset of client electronic device 28, 30, 32, 34 and may select 452 a disrupter for inclusion within alertness test 100 based, at least in part, upon the environmental variables monitored 450 concerning the user.

For example, impairment detection process 10 may monitor 450 the forward-facing camera (i.e., the camera facing the user) included within the client electronic device to look for signs of impairment of the user (e.g., bloodshot eyes and/or dilated pupils). In response to detecting such signs of impairment, impairment detection process 10 may select 452 a disrupter that is effective at detecting impairment. Impairment detection process 10 may then administer 454 an alertness test to the user (regardless of whether or not to the user had previously taken an alertness test).

Further, impairment detection process 10 may monitor 450 the clock included within the client electronic device to determine if the user (e.g., user 36, 38, 40, 42) has been working for an extended period of time (e.g., 12 hours). In response to determining that the user has been working for an extended period of time, impairment detection process 10 may select 452 a disrupter that is effective at detecting fatigue. Impairment detection process 10 may then administer 454 an alertness test to the user (regardless of whether or not to the user had previously taken an alertness test).

Additionally, impairment detection process 10 may monitor 450 the GPS chipset included within the client electronic device to determine the location of the user (e.g., user 36, 38, 40, 42). In response to determining that e.g., the user has moved from a lower-risk area to a higher risk area within a factory, impairment detection process 10 may select 452 a disrupter that checks for the level of alertness required for the higher risk area within the factory. Impairment detection process 10 may then administer 454 an alertness test to the user (regardless of whether or not to the user had previously taken an alertness test).

Geo-Fencing:

As discussed above, impairment detection process 10 may be configured to administer various implementations of alertness test 100. Further and when administering alertness test 10, impairment detection process 10 may: render a plurality of objects for use within alertness test 100 being administered to a user (e.g., user 36, 38, 40, 42); render a disrupter (e.g., disrupter 232, 236) configured to distract the user; solicit a response from the user concerning the plurality of objects; receive the response from the user; and determine a result for the user based (at least in part) upon the response received from the user.

Further and as discussed above, impairment detection process 10 may be configured to establish a baseline for each type of task that a user may perform. For example, the same construction work may be required to have a higher level of alertness when operating a crane then when driving a pickup truck. Additionally, different levels of alertness may be required when performing the same task at different geographic locations. For example, when a user (e.g., user 36, 38, 40, 42) is driving a quarry dump truck within a strip mine, a first level of alertness may be required. But when the same user is driving that same quarry dump truck on a public road to transport the quarry dump truck from one mining facility to another mining facility, the user may be required to have a higher level of alertness.

Figure 8:
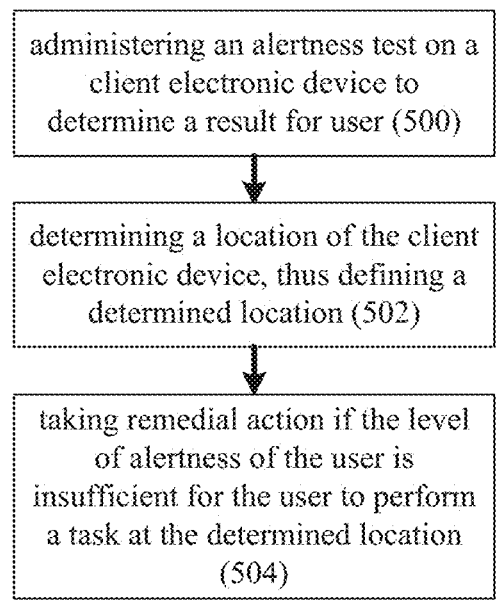
FIG. 8 is a flowchart of another embodiment of the impairment detection process of FIG. 1 according to an embodiment of the present disclosure.

Accordingly and referring also to FIG. 8, impairment detection process 10 may administer 500 an alertness test (e.g., alertness test 100) on a client electronic device (e.g., client electronic device 28, 30, 32, 34) to determine a result (e.g., result 102) for user (e.g., user 36, 38, 40, 42), wherein result 102 may be indicative of a level of alertness of the user.

Impairment detection process 10 may determine 502 a location of the client electronic device, thus defining a determined location. For example, impairment detection process 10 may monitor the GPS chipset included within the client electronic device to determine 502 the location of the client electronic device. Alternatively, cell tower triangulation location methodologies or wifi signal strength location methodologies may be utilized to determine 502 the location of the client electronic device. Impairment detection process 10 may then take 504 remedial action if the level of alertness of the user is insufficient for the user to perform a task at the determined location of the client electronic device.

For example, impairment detection process 10 may determine 502 the location of the client electronic device (and, therefore, the location of the user of the client electronic device) during the performance of a specific task and determine whether remedial action needs to be taken 504. Accordingly, assume that impairment detection process 10 administers 500 alertness test 100 on a client electronic device (e.g., client electronic device 28, 30, 32, 34) to determine if the user has a sufficient level of alertness to (in this example) drive a quarry dump truck within a mining facility. Further, assume that the user is deemed to have the requisite level of alertness by impairment detection process 10.

Assume that the user performs the task of driving the quarry dump truck within the mining facility. Impairment detection process 10 may monitor the location of the client electronic device (which may be included within (or rigidly affixed to) the quarry dump truck) to determine 502 a location for the client electronic device (thus defining a determined location). As discussed above, impairment detection process 10 may monitor a GPS chipset included within the client electronic device.

Continuing with the above-stated example, assume that it is subsequently determined (e.g., through GPS tracking) that the user is now driving the quarry dump truck outside of the mining facility, which requires a higher level of alertness (due to the enhanced level of risk) that exceeds the level of alertness required for the user to drive the quarry dump truck inside the mining facility. Accordingly, impairment detection process 10 may take 504 remedial action since the level of alertness of the user is insufficient for the user to perform the current task (e.g., drive a quarry dump truck) at the determined location of the client electronic device (e.g., outside of the mining facility).

Examples of such remedial action may include but are not limited to: writing an entry into a log file (e.g., writing about the incident in a personnel log file associated with the user), notifying a supervisor of the user (e.g., via automated voice call, text message or email that the user does not have the appropriate level of alertness), sounding an alarm (e.g., indicating that a deficient level of alertness situation is occurring), disabling a piece of equipment being utilized by the user (e.g., disabling the quarry dump truck), and notifying the user that they need to take another alertness test.

Biometric Interface:

As discussed above, impairment detection process 10 may be configured to administer various implementations of alertness test 100. Further and when administering alertness test 100, impairment detection process 10 may: render a plurality of objects for use within alertness test 100 being administered to a user (e.g., user 36, 38, 40, 42); render a disrupter (e.g., disrupter 232, 236) configured to distract the user; solicit a response from the user concerning the plurality of objects; receive the response from the user; and determine a result for the user based (at least in part) upon the response received from the user.

Additionally, impairment detection process 10 may be configured to interface with biometric device 130 so that result 102 of the above-described alertness test (e.g., alertness test 100) may be adjusted (upward or downward) based upon biometric information 132 provided by biometric device 130.

Figure 9:
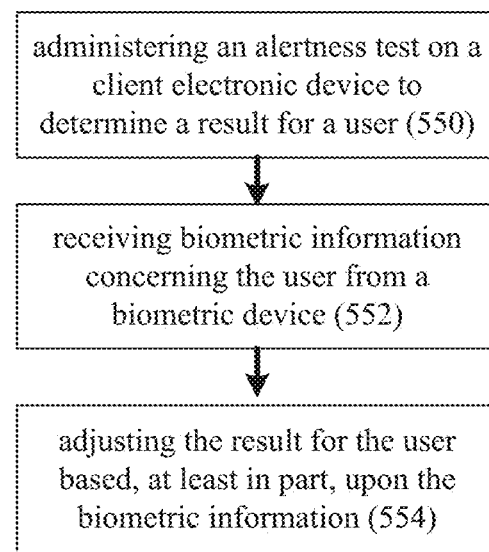
FIG. 9 is a flowchart of another embodiment of the impairment detection process of FIG. 1 according to an embodiment of the present disclosure.

Accordingly and referring also to FIG. 9, impairment detection process 10 may administer 550 an alertness test (e.g., alertness test 120) on a client electronic device (e.g., client electronic device 28, 30, 32, 34) to determine a result (e.g., result 120) for a user (e.g., user 36, 38, 40, 42), wherein result 120 may be indicative of a level of alertness of the user.

Impairment detection process 10 may receive 552 biometric information 132 concerning the user from biometric device 130. Biometric information 132 may concern one or more health aspects of the user such as: a pulse rate of the user; a blood glucose level of the user; and a blood oxygen level of the user. Accordingly, examples of biometric device 130 may include but are not limited to: a heart rate monitoring device, a blood glucose monitoring device, and a blood oxygen monitoring device. Impairment detection process 10 may then adjust 554 the result for the user based, at least in part, upon the biometric information.

For example, assume that impairment detection process 10 administers 550 alertness test 120 on a client electronic device (e.g., client electronic device 28, 30, 32, 34) to determine if a user has the requisite level of alertness to fly a Boeing 737. Further assume that impairment detection process 10 determines that the user does indeed have the requisite level of alertness. However, assume that impairment detection process 10 receives 552 biometric information 132 from biometric device 130 (e.g., a blood glucose monitoring device) that indicates that the blood glucose level of the user is 70 milligrams per deciliter (i.e., 30 milligrams per deciliter below normal). Accordingly, while the user may currently have an acceptable level of alertness, they may not in the immediate future, since the user may be deemed susceptible to lightheadedness. Accordingly, impairment detection process 10 may adjust 554 the result for the user downward based upon this blood glucose reading and conclude that the user is not fit to fly (i.e., the user does not have the requisite level of alertness).

Cognitive Degeneration Tracking:

As discussed above, impairment detection process 10 may be configured to administer various implementations of alertness test 100. Further and when administering alertness test 10, impairment detection process 10 may: render a plurality of objects for use within alertness test 100 being administered to a user (e.g., user 36, 38, 40, 42); render a disrupter (e.g., disrupter 232, 236) configured to distract the user; solicit a response from the user concerning the plurality of objects; receive the response from the user; and determine a result for the user based (at least in part) upon the response received from the user. Further and as discussed above, impairment detection process 10 may be configured to calculate a baseline for a user (e.g., user 36, 38, 40, 42) with respect to alertness test 100.

Figure 10:
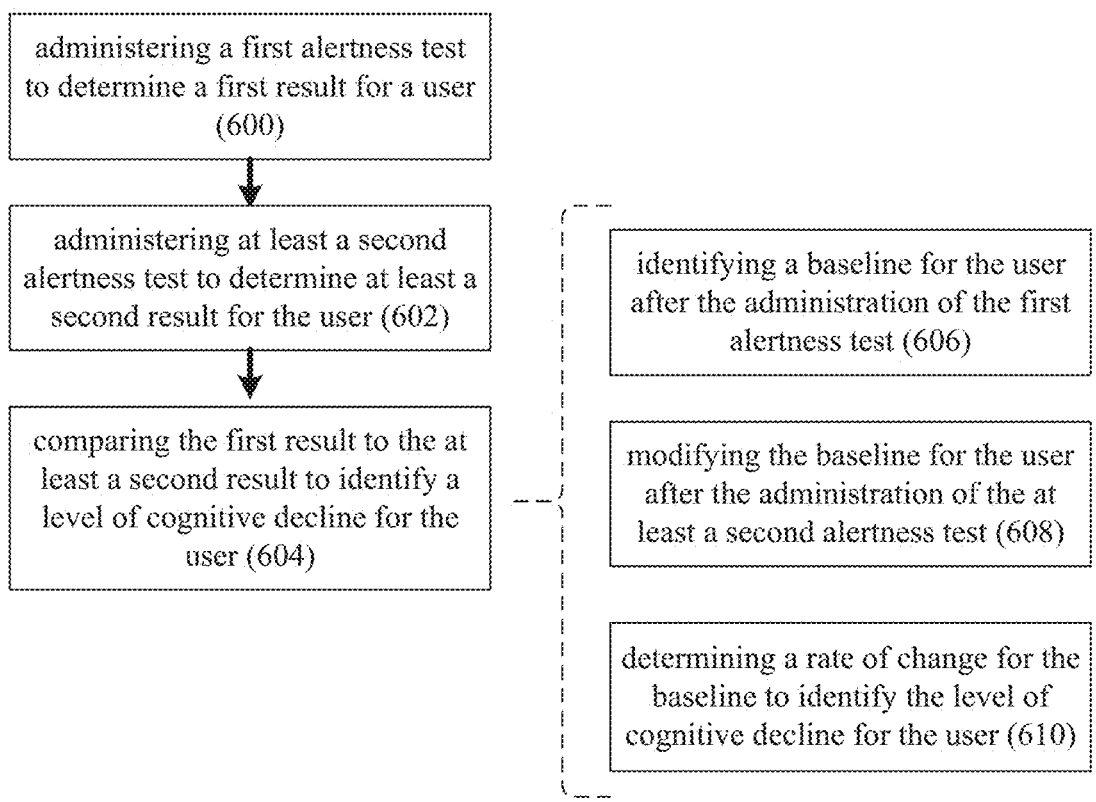
FIG. 10 is a flowchart of another embodiment of the impairment detection process of FIG. 1 according to an embodiment of the present disclosure.

Accordingly and referring also to FIG. 10, impairment detection process 10 may administer 600 a first alertness test (e.g., alertness test 100) to determine a first result (e.g., result 102) for a user (e.g., user 36, 38, 40, 42), wherein this first result may be indicative of a first level of alertness of the user at the time of the first alertness test.

Impairment detection process 10 may administer 602 at least a second alertness test (e.g., alertness test 100) to determine at least a second result (not shown) for the user (e.g., user 36, 38, 40, 42), wherein the at least a second result may be indicative of at least a second level of alertness of the user at the time of the at least a second alertness test.

Impairment detection process 10 may then compare 604 the first result (e.g., result 120) to the at least a second result (not shown) to identify a level of cognitive decline for the user, wherein the level of cognitive decline for the user may be indicative of a cognitive disorder (e.g., Delirium, Dementia, Amnesia).

For example, when comparing 604 the first result (e.g., result 120) to the at least a second result (not shown) to identify a level of cognitive decline for the user, impairment detection process 10 may: identify 606 a baseline (in the manner described above) for the user after the administration of the first alertness test; modify 608 the baseline (in the manner described above) for the user after the administration of the at least a second alertness test; and determine 610 a rate of change (e.g., a first order derivative) for the baseline to identify the level of cognitive decline for the user. For example, if the level of cognitive decline exceeds a certain percentage over a unit time, the user may be deemed to be suffering from a cognitive disorder. Additionally/alternatively and for users that have already been diagnosed with a cognitive disorder, the rate of advancement of the cognitive disorder (and the long term cognitive performance) may be monitored via impairment detection process 10.

Forward Circadian Projection:

As discussed above, impairment detection process 10 may be configured to administer various implementations of alertness test 100. Further and when administering alertness test 10, impairment detection process 10 may: render a plurality of objects for use within alertness test 100 being administered to a user (e.g., user 36, 38, 40, 42); render a disrupter (e.g., disrupter 232, 236) configured to distract the user; solicit a response from the user concerning the plurality of objects; receive the response from the user; and determine a result for the user based (at least in part) upon the response received from the user. Further and as discussed above, impairment detection process 10 may be configured to calculate a baseline for a user (e.g., user 36, 38, 40, 42) with respect to alertness test 100.

As is known, a circadian rhythm is a roughly twenty-four hour cycle in the physiological processes of living beings, including humans, plants, and animals. In a strict sense, circadian rhythms are endogenously generated, although they can be modulated by external cues such as sunlight and temperature, wherein these circadian rhythms generally defines the sleep patterns and sleep needs of (in this example) a user.

Figure 11:
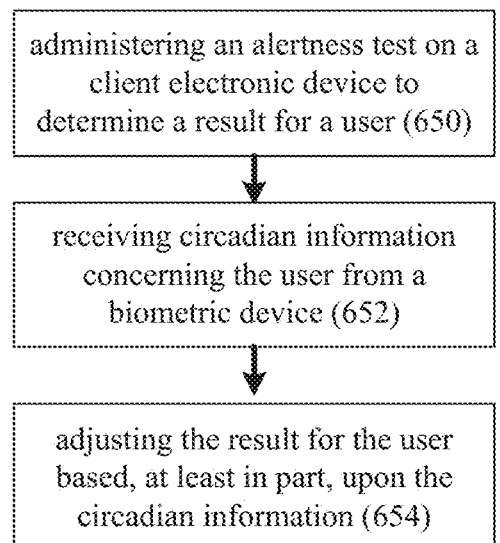
FIG. 11 is a flowchart of another embodiment of the impairment detection process of FIG. 1 according to an embodiment of the present disclosure.

Accordingly and referring also to FIG. 11, impairment detection process 10 may administer 650 an alertness test (e.g., alertness test 100) on a client electronic device (e.g., client electronic device 28, 30, 32, 34) to determine a result (e.g., result 120) for a user (e.g., user 36, 38, 40, 42), wherein the result may be indicative of a level of alertness of the user.

Impairment detection process 10 may receive 652 circadian information 134 concerning the user. As discussed above, circadian information 134 may concern historical sleep patterns of the user. Circadian information 134 may be based, at least in part, upon one or more of biometric information 132 obtained from biometric device 130, a questionnaire (e.g., an electronic survey) filled out by the user, and a work schedule for the user. Impairment detection process 10 may then adjust 654 result 120 for the user based, at least in part, upon circadian information 134.

For example, assume that impairment detection process 10 administers 650 alertness test 120 on a client electronic device (e.g., client electronic device 28, 30, 32, 34) to determine if a user has the requisite level of alertness to operate a crane. Further assume that impairment detection process 10 determines that the user does indeed have the requisite level of alertness. However, assume that impairment detection process 10 receive 652 circadian information 134 that indicates that the user almost always works a 6:00 a.m. to 6:00 p.m. shift and, therefore, it is understood that the user sleeps sometime between 6:00 p.m. and 6:00 a.m. Further assume that it is 10:00 p.m. and, therefore, it is likely that during the time the user would be operating the crane, the user would typically be sleeping. Accordingly, while the user may currently have an acceptable level of alertness, they may not in the immediate future, since the user may likely get tired or drowsy. Accordingly, impairment detection process 10 may adjust 654 result 120 for the user based, at least in part, upon circadian information 134 and conclude that the user is not fit to operate a crane (i.e., the user does not have the requisite level of alertness).

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
   monitoring one or more environmental variables concerning a client electronic device configured to administer an alertness test to a user, wherein monitoring the one or more environmental variables concerning the client electronic device includes:
      monitoring a microphone included within the client electronic device, and
      determining a noise level for an environment associated with the client electronic device;
   selecting a disrupter for inclusion within the alertness test based, at least in part, upon the one or more environmental variables concerning the client electronic device, wherein selecting the disrupter includes:
      selecting a first disrupter in response to determining a first noise level for the environment associated with the client electronic device, and
      selecting a second disrupter in response to determining a second noise level for the environment associated with the client electronic device;
   rendering, on a graphical user interface of the client electronic device, a plurality of objects for use within the alertness test being administered to the user;
   rendering, on the graphical user interface of the client electronic device, the selected disrupter configured to distract the user;
   soliciting, via the graphical user interface of the client electronic device, a response from the user concerning the plurality of objects;
   determining a result for the user based, at least in part, upon the response solicited from the user;
   receiving, from a biometric device, biometric data concerning the user;
   adjusting the result for the user based upon, at least in part, the biometric data received from the biometric device; and
   determining a level of alertness for the user based upon, at least in part, the adjusted result for the user.

2. The computer-implemented method of claim 1 wherein the disrupter includes one or more of:
   a visual disrupter;
   an audible disrupter; and
   a physical disrupter.

3. The computer-implemented method of claim 1 wherein monitoring one or more environmental variables concerning a client electronic device includes:
   monitoring a camera included within the client electronic device.

4. The computer-implemented method of claim 1 wherein monitoring one or more environmental variables concerning a client electronic device includes:
   monitoring a GPS chipset included within the client electronic device.

5. A computer program product residing on a non-transitory computer readable medium having a plurality of instructions stored thereon which, when executed by a processor, cause the processor to perform operations comprising:
   monitoring one or more environmental variables concerning a client electronic device configured to administer an alertness test to a user, wherein monitoring the one or more environmental variables concerning the client electronic device includes:
      monitoring a microphone included within the client electronic device, and
      determining a noise level for an environment associated with the client electronic device;
   selecting a disrupter for inclusion within the alertness test based, at least in part, upon the one or more environmental variables concerning the client electronic device, wherein selecting the disrupter includes:
      selecting a first disrupter in response to determining a first noise level for the environment associated with the client electronic device, and
      selecting a second disrupter in response to determining a second noise level for the environment associated with the client electronic device;

rendering, on a graphical user interface of the client electronic device, a plurality of objects for use within the alertness test being administered to the user;

rendering, on the graphical user interface of the client electronic device, the selected disrupter configured to distract the user;

soliciting, via the graphical user interface of the client electronic device, a response from the user concerning the plurality of objects;

determining a result for the user based, at least in part, upon the response solicited from the user;

receiving, from a biometric device, biometric data concerning the user;

adjusting the result for the user based upon, at least in part, the biometric data received from the biometric device; and determining a level of alertness for the user based upon, at least in part, the adjusted result for the user.

6. The computer program product of claim 5 wherein the disrupter includes one or more of:

a visual disrupter;

an audible disrupter; and a physical disrupter.

7. The computer program product of claim 5 wherein monitoring one or more environmental variables concerning a client electronic device includes:

monitoring a camera included within the client electronic device.

8. The computer program product of claim 5 wherein monitoring one or more environmental variables concerning a client electronic device includes:

monitoring a GPS chipset included within the client electronic device.

9. A computing system including a processor and memory configured to perform operations comprising:

monitoring one or more environmental variables concerning a client electronic device configured to administer an alertness test to a user, wherein monitoring the one or more environmental variables concerning the client electronic device includes:

monitoring a microphone included within the client electronic device, and determining a noise level for an environment associated with the client electronic device;

selecting a disrupter for inclusion within the alertness test based, at least in part, upon the one or more environmental variables concerning the client electronic device, wherein selecting the disrupter includes:

selecting a first disrupter in response to determining a first noise level for the environment associated with the client electronic device, and selecting a second disrupter in response to determining a second noise level for the environment associated with the client electronic device;

rendering, on a graphical user interface of the client electronic device, a plurality of objects for use within the alertness test being administered to the user;

rendering, on the graphical user interface of the client electronic device, the selected disrupter configured to distract the user;

soliciting, via the graphical user interface of the client electronic device, a response from the user concerning the plurality of objects;

determining a result for the user based, at least in part, upon the response solicited from the user;

receiving, from a biometric device, biometric data concerning the user;

adjusting the result for the user based upon, at least in part, the biometric data received from the biometric device; and determining a level of alertness for the user based upon, at least in part, the adjusted result for the user.

10. The computing system of claim 9 wherein the disrupter includes one or more of:

a visual disrupter;

an audible disrupter; and a physical disrupter.

11. The computing system of claim 9 wherein monitoring one or more environmental variables concerning a client electronic device includes:

monitoring a camera included within the client electronic device.

12. The computing system of claim 9 wherein monitoring one or more environmental variables concerning a client electronic device includes:

monitoring a GPS chipset included within the client electronic device.

* * * * *